United States Patent [19]
Stürmer et al.

[11] Patent Number: 6,136,986
[45] Date of Patent: Oct. 24, 2000

[54] PROCESS FOR PREPARING SUBSTITUTED CHROMAN DERIVATIVES

[75] Inventors: Rainer Stürmer, Rödersheim-Gronau; Kai-Uwe Baldenius, Frankenthal, both of Germany

[73] Assignee: BASF Aktiengesellschaft, Ludwigshafen, Germany

[21] Appl. No.: 09/459,727

[22] Filed: Dec. 13, 1999

[30] Foreign Application Priority Data

Dec. 22, 1998 [DE] Germany ............................ 198 59 251

[51] Int. Cl.$^7$ ....................... C07D 311/58; C07D 311/66; C07D 309/30
[52] U.S. Cl. ........................ 549/405; 549/406; 549/407; 549/416; 549/419; 549/420; 549/423
[58] Field of Search .................... 549/405, 406, 549/407, 416, 419, 420, 423

[56] References Cited

U.S. PATENT DOCUMENTS

| | | | |
|---|---|---|---|
| 2,411,969 | 12/1946 | Karrer et al. | 260/333 |
| 2,514,168 | 7/1950 | Smith et al. | 260/333 |
| 3,947,473 | 3/1976 | Scott et al. | 260/345 |

FOREIGN PATENT DOCUMENTS

| | | |
|---|---|---|
| 2364141 | 6/1974 | Germany . |
| WO98/11197 | 3/1998 | WIPO . |

OTHER PUBLICATIONS

T. Netscher, "Stereoisomers of Tocopherols–Synthesis and Analytics", Chimia 50, (1996), pp. 563–568.

H. Mayer et al., "Helvetica Chimica Acta", vol. XLVI, (1963), pp. 650–671.

J. Scott et al., "6–Hydroxychroman–2carboxylic Acids" Novel Antioxidants, J. Am. Oil Chemist Soc., vol. 51 No. 1 (1974), pp. 201–203.

B.P. Mundy et al., "A Synthesis of Frontalin and Brevicomin", J. Org. Chem, vol. 36, No. 16, (1971) p. 2390.

J.G. Jun et al., "Ketal–Lactone Compounds and their Stereoselective Cleavage to Cyclic Ethers", Tetrahedron Letters, vol. 38, No. 47, (1997), pp. 8207–8210.

B.P. Mundy et al., "Chemistry of the 6, 8–Dioxabicyclo [3.2.1]Octane Series Sources, Synthesis, Structures and Reactions", Heterocycles, vol.6, No.1, (1977), pp. 51–76.

D.L. Boger et al. "Hetero–Diels–Alder–Methodology in Organic Synthesis", (1987), pp. 185–187.

S. Murai et al. "Two Types of Indirect Cyclodimerization of Biacetyl Via Its Enol Silyl Ethers", Chemistry Letters (1977) pp. 1219–1222.

K. Takaki et al. "Cycloaddition Reactions of 3-(Phenylthio)-3-buten-2-one: Synthesis of Functionalized Dihydropyran Derivatives and Their Ring–Opening Reaction", J. Org. Chem, vol. 47, No. 24, (1982), pp. 5246–5250.

W. Gore et al. "Regiospecificity of the 1,4 Cycloaddition of 2–Methyl–1–penten–3–one to Methyl Crotonate and to Methyl Methacrylate", J. Org. Chem., vol. 41, No. 4, (1976), pp. 603–607.

C.W. Smith et al., "Reactions of Acrolein and Related Compounds I. Addition of Vinyl Ehters", J. Am. Chem. Soc., vol. 73, (1951), pp. 5267–5272.

R. Funk et al. "Preparation and Diels–Alder Cycloaddition of 2–Acyloxyacroleins. Facile Synthesis of Functionalized Taxol A–Ring Synthons" J. Org. Chem., vol. 61, (1996), pp. 2598–2599.

*Primary Examiner*—Bernard Dentz
*Attorney, Agent, or Firm*—Keil & Weinkauf

[57] ABSTRACT

The invention relates to a process for preparing substituted chroman derivatives of the general formula VII,

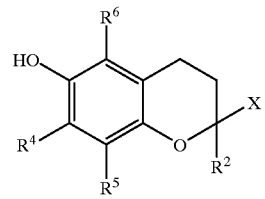

VII where

X is the group —CN, —COOR$^3$, —CHO, —CH$_2$OR$^7$ or —CH(OR$^8$)$_2$,

R$^2$ is a C$_1$–C$_{23}$-alkyl, C$_2$–C$_{23}$-alkenyl, C$_6$–C$_{18}$-aryl or C$_7$–C$_{18}$-aralkyl radical, R$^3$ is hydrogen or an optionally substituted C$_1$–C$_4$-alkyl radical, R$^4$, R$^5$, R$^6$ are, independently of one another, hydrogen or a C$_1$–C$_4$-alkyl radical, R$^7$ is hydrogen or a C$_1$–C$_4$-alkyl radical, R$^8$ is a C$_1$–C$_4$-alkyl radical, or the two radicals are a C$_2$–C$_6$-alkylene radical which links the two oxygen atoms to form a cyclic acetal and is optionally branched or may carry one or two carboxyl groups, cyclohexyl or phenyl radicals, and to the novel intermediates of the process.

11 Claims, No Drawings

PROCESS FOR PREPARING SUBSTITUTED CHROMAN DERIVATIVES

The invention relates to a process for preparing substituted chroman derivatives of the general formula VII,

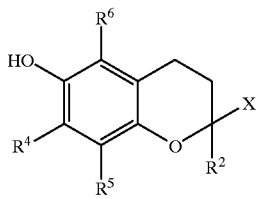

VII where
- X is the group —CN, —COOR$^3$, —CHO, —CH$_2$OR$^7$ or —CH(OR$^8$)$_2$,
- R$^2$ is a C$_1$–C$_{23}$-alkyl, C$_2$–C$_{23}$-alkenyl, C$_6$–C$_{18}$-aryl or C$_7$–C$_{18}$-aralkyl radical,
- R$^3$ is hydrogen, a C$_1$–C$_4$-alkyl radical, a C$_1$–C$_4$-haloalkyl radical, a C$_1$–C$_4$-hydroxyalkyl radical or a C$_1$–C$_4$-aminoalkyl radical,
- R$^4$, R$^5$, R$^6$ are, independently of one another, hydrogen or a C$_1$–C$_4$-alkyl radical,
- R$^7$ is hydrogen or a C$_1$–C$_4$-alkyl radical,
- R$^8$ is a C$_1$–C$_4$-alkyl radical, or the two radicals are a C$_2$–C$_6$-alkylene radical which links the two oxygen atoms to form a cyclic acetal and is optionally branched or may carry one or two carboxyl groups, cyclohexyl or phenyl radicals, and to the novel intermediates for the process.

The substituted chroman derivatives of the general formula VII are known intermediates in demand for pharmaceutical agents and vitamins (e.g. tocopherol). Starting from 6-acetyloxychroman-2-aldehyde it has been possible to prepare, inter alia, α-tocopherol by a Wittig reaction with a phosphonium salt (T. Netscher, Chimia 1996, 50, 563–567; H. Mayer, P. Schudel, R. Ruegg, O. Isler, Helv. Chim. Acta 1963, 46, 650). In addition, these compounds, e.g. the 6-hydroxychroman-2-carboxylic acids, themselves have an antioxidant effect in animal fat, vegetable oils and emulsions (J. W. Scott et al., J. of the American Oil Chemists Society, 1974, 51, 200–203).

The preparation of substituted chroman derivatives by condensation of the corresponding hydroquinones with allyl alcohols has been disclosed (U.S. Pat. No 2,411,969, WO 9821197 A2).

In addition, DE 2364141 A1 describes a similar approach by reaction of a hydroquinone with unsaturated ketones or acetals in the presence of an acid.

It is common to all the processes described to date that the aromatic system is employed as synthon and the pyran moiety is subsequently built on by electrophilic aromatic substitution.

These reactions have the disadvantage that chromans unsubstituted in the aromatic system are difficult to prepare because these electron-rich aromatic systems are prone to multiple alkylation.

Moreover, with different alkyl groups on the aromatic system, regioselectivity problems arise in the abovementioned syntheses, i.e. it is not possible to prepare all desired substitution patterns on the aromatic moiety in the chroman structure equally satisfactorily.

It is an object of the present invention to develop a process for preparing the chroman derivatives which is more flexible in terms of the substituents, is economical and proceeds via easily handled intermediates and reagents.

We have found that this object is achieved in that the chroman derivatives of the general formula VII mentioned at the outset can be prepared by a multistage process, which comprises, in a first step, reacting substituted acroleins of the general formula I,

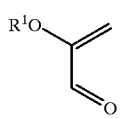

I where
R$^1$ is a C$_1$–C$_4$-alkyl, C$_6$–C$_{18}$-aryl, C$_7$–C$_{18}$-aralkyl, C$_1$–C$_4$-acyl, a halogenated C$_1$–C$_4$-acyl radical or another acid-labile protective group for the hydroxyl group, with acrylonitriles, acrylates, acroleins, acrolein acetals, allyl alcohols or allyl ethers of the general formula II

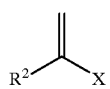

II to give the corresponding 3,4-dihydro-2H-pyrans of the general formula III

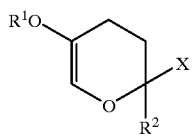

III and, in a second step, reacting the latter with an acid to give the corresponding 5-oxotetrahydropyrans of the general formula IV

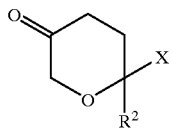

IV and, in a third step, reacting the latter with substituted vinyl ketones of the general formula V

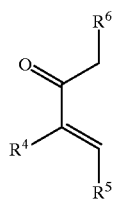

V to give the corresponding chromen-6-one derivatives of the general formula VI

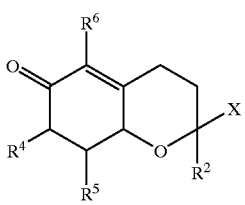

VI and, in a 4th step, dehydrogenating the latter to give the substituted chroman derivatives of the general formula VII.

The starting materials for the process are substituted acroleins of the general formula I and acrylonitriles, acrylates, acroleins, acrolein acetals, allyl alcohols or allyl ethers of the general formula II.

The substituted acroleins of the general formula I in the first step of the process according to the invention are the diene component in a hetero-Diels-Alder reaction.

The $R^1$ radical in the substituted acroleins can be a $C_1$–$C_4$-alkyl, $C_6$–$C_{18}$-aryl, $C_7$–$C_{18}$-aralkyl, an optionally halogenated $C_1$–$C_4$-acyl radical or another acid-labile protective group for the hydroxyl group. A $C_1$–$C_4$-alkyl radical means a methyl, ethyl, n-propyl, i-propyl, n-butyl, i-butyl or t-butyl radical, with methyl being preferred. Examples of $C_6$–$C_{18}$-aryl radicals are phenyl, naphthyl or phenyl which is optionally substituted one to three times by $C_1$–$C_4$-alkyl radicals. $C_7$–$C_{18}$-Aralkyl radicals mean radicals such as benzyl or phenylethyl.

Examples of $C_1$–$C_4$-acyl radicals or halogenated $C_1$–$C_4$-acyl radicals, i.e. those substituted by one to three identical or different halogen radicals such as Cl, Br, I or F, are acetyl, monochloro-, dichloro- or trichloroacetyl, trifluoroacetyl, propionyl or butyryl.

$R^1$ can also be another acid-labile protective group for the hydroxyl group of the enol. It is possible in principle to use any acid-labile protective group. Preferred acid-labile protective groups are the acid-labile protective groups for hydroxyl groups disclosed in the literature (T. W. Greene, Protective Groups in Organic Synthesis, John Wiley & Sons New York, 1981, pages 14–71; P. J. Kocienski, Protecting Groups, Georg Thieme Verlag Stuttgart, 1994, pages 21–94). Particularly preferred acid-labile protective groups are esters such as phenylacetates, triphenylmethoxyacetate, phenoxyacetates, halophenoxyacetates, haloalkylphenoxyacetates, formate, benzoylformate, 3-phenylpropionate, isobutyrate, pivaloate, adamantoate, crotonates or benzoates;

or aliphatic and aromatic ethers such as methyl, benzyl, o-nitrobenzyl, p-methoxybenzyl, 3,4-dimethoxybenzyl ethers, trityls, p-methoxyphenyl(diphenyl)methyl, 4,4', 4"-tris(benzoyloxy)trityl, di(p-methoxyphenyl)phenylmethyl, tert-butyls, 9-phenyl-9-xanthenyl, allyls, 2-(trimethylsilyl)ethyl.

Preferred substituted acroleins of the general formula I are α-methoxyacrolein, α-benzyloxyacrolein or acetoxyacrolein.

The substituted acrylonitriles (X=—CN), acroleins (X=—CHO), acrylates (X=—COOR$^3$), acrolein acetals (X=—CH(OR$^8$)$_2$), allyl ethers (X=—CH$_2$OR$^7$) or allyl alcohols (X=—CH$_2$OR$^7$; R$^7$=hydrogen) of the general formula II in the first step of the process according to the invention are the ene component in a hetero-Diels-Alder reaction.

The $R^2$ radical can be a $C_1$–$C_{23}$-alkyl radical such as methyl, ethyl, n-propyl, i-propyl, n-Butyl, i-butyl, t-butyl, pentyl, hexyl, heptyl, octyl, nonyl or 4,8,12-trimethyltridecyl, in particular methyl, a $C_2$–$C_{23}$-alkenyl radical such as ethenyl(vinyl), propenyl (allyl), 4-methyl-3-pentenyl, 4,8-dimethyl-3,7-nonadienyl or 4,8,12-trimethyl-3,7,11-tridecatrienyl, a $C_6$–$C_{18}$-aryl radical as mentioned above for $R^1$, in particular phenyl, or a $C_7$–$C_{18}$-aralkyl radical as mentioned above for $R^1$, in particular benzyl.

Preferred $R^2$-substituted acrylonitriles (X=—CN) of the formula II are 2-methylacrylonitrile, 2-(4,8,12-trimethyltridecyl)-acrylonitrile, 2-(4-methyl-3-pentenyl)acrylonitrile, 2-(4,8-dimethyl-3,7-nonadienyl)acrylonitrile or 2-(4,8,12-trimethyl-3,7,11-tridecatrienyl)acrylonitrile.

Preferred $R^2$-substituted acroleins (X=—CHO) of the formula II are 2-methylacrolein (methacrolein), 2-(4,8,12-trimethyl-tridecyl)acrolein, 2-(4-methyl-3-pentenyl)acrolein, 2-(4,8-dimethyl-3,7-nonadienyl)acrolein or 2-(4,8,12-trimethyl-3,7,11-tridecatrienyl)acrolein.

$R^2$-substituted acrylates (X=—COOR$^3$) mean substituted acrylic acids ($R^3$=hydrogen) or acrylic esters ($R^3$=a $C_1$–$C_4$-alkyl radical, a $C_1$–$C_4$-haloalkyl radical, a $C_1$–$C_4$-hydroxyalkyl radical or a $C_1$–$C_4$-aminoalkyl radical).

$C_1$–$C_4$-Alkyl radicals for $R^3$ mean the $C_1$–$C_4$-alkyl radicals mentioned above for $R^1$, in particular methyl or ethyl.

$C_1$–$C_4$-Haloalkyl radicals mean $C_1$–$C_4$-alkyl radicals substituted by one to three identical or different halogen radicals such as F, Cl, Br or I. Examples of $C_1$–$C_4$-haloalkyl radicals are 2-chloroethyl, 1,2-dichloroethyl or 2,2,2-trichloroethyl and the corresponding bromoethyl radicals.

$C_1$–$C_4$-Hydroxyalkyl radicals mean $C_1$–$C_4$-alkyl radicals substituted by one to three hydroxyl groups. Examples of $C_1$–$C_4$-hydroxyalkyl radicals are 2-hydroxyethyl or 1,2-dihydroxyethyl.

$C_1$–$C_4$-Aminoalkyl radicals mean $C_1$–$C_4$-alkyl radicals substituted by one to three amino groups. Amino groups mean NH$_2$ groups, mono($C_1$–$C_4$-)alkylamino groups or di($C_1$–$C_4$-)alkylamino groups. Examples of $C_1$–$C_4$-aminoalkyl radicals are aminoethyl, 2-methylaminoethyl, 2-dimethylaminoethyl or ethylmethylaminoethyl.

Preferred substituted acrylates of the general formula II are 2-methylacrylic acid (methacrylic acid), methyl methacrylate, ethyl methacrylate, 2-hydroxyethyl methacrylate, 2-chloroethyl methacrylate, 2-dimethylaminoethyl methacrylate, 2-(4,8,12-trimethyltridecyl)acrylic acid, 2-(4-methyl-3-pentenyl)-acrylic acid, 2-(4,8-dimethyl-3,7-nonadienyl)acrylic acid, 2-(4,8,12-trimethyl-3,7,11-tridecatrienyl)acrylic acid, methyl 2-(4,8,12-trimethyltridecyl)acrylate, methyl 2-(4-methyl-3-pentenyl)acrylate, methyl 2-(4,8-dimethyl-3,7-nonadienyl)acrylate, methyl 2-(4,8,12-trimethyl-3,7,11-tridecatrienyl)acrylate, ethyl 2-(4,8,12-trimethyltridecyl)acrylate, ethyl 2-(4-methyl-3-pentenyl)acrylate, ethyl 2-(4,8-dimethyl-3,7-nonadienyl)acrylate, ethyl 2-(4,8,12-trimethyl-3,7,11-tridecatrienyl)acrylate, 2-hydroxyethyl 2-(4,8,12-trimethyltridecyl)acrylate, 2-hydroxyethyl 2-(4-methyl-3-pentenyl)acrylate, 2-hydroxyethyl 2-(4,8-dimethyl-3,7-nonadienyl)acrylate, 2-hydroxyethyl 2-(4,8,12-trimethyl-3,7,11-tridecatrienyl)acrylate, 2-chloroethyl 2-(4,8,12-trimethyltridecyl)acrylate, 2-chloroethyl) 2-(4-methyl-3-pentenyl)acrylate, 2-chloroethyl 2-(4,8-dimethyl-3,7-nonadienyl)acrylate or 2-chloroethyl 2-(4,8,12-trimethyl-3,7,11-tridecatrienyl)acrylate, 2-dimethylamino ethyl 2-(4,8,12-trimethyltridecyl)acrylate, 2-dimethylaminoethyl 2-(4-methyl-3-pentenyl)acrylate, 2-dimethylaminoethyl 2-(4,8-dimethyl-3,7-nonadienyl)acrylate or 2-dimethylaminoethyl 2-(4,8,12-trimethyl-3,7,11-tridecatrienyl)- acrylate.

In the case of the $R^2$-substituted allyl ethers ($X$=—$CH_2OR^7$) or allyl alcohols ($X$=—$CH_2OR^7$; $R^7$=hydrogen), $R^7$ can be hydrogen or a $C_1$–$C_4$-alkyl radical as described above for $R^1$, in particular methyl or ethyl.

Preferred substituted allyl ethers of the general formula II are 2-methyl-3-methoxypropene, 2-methyl-3-ethoxypropene, 2-(4,8,12-trimethyltridecyl)-3-methoxypropene, 2-(4-methyl-3-pentenyl)-3-methoxypropene, 2-(4,8-dimethyl-3,7-nonadienyl)-3-methoxypropene, 2-(4,8,12-trimethyl-3,7,11-tridecatrienyl)-3-methoxypropene, 2-(4,8,12-trimethyltridecyl)-3-ethoxypropene, 2-(4-methyl-3-pentenyl)-3-ethoxypropene, 2-(4,8-dimethyl-3,7-nonadienyl)-3-ethoxypropene or 2-(4,8,12-trimethyl-3,7,11-tridecatrienyl)-3-ethoxypropene.

Preferred substituted allyl alcohols of the general formula II are 2-methyl-2-propen-1-ol (2-methylallyl alcohol, methallyl alcohol), 2-(4,8,12-trimethyltridecyl)-2-propen-1-ol, 2-(4-methyl-3-pentenyl)-2-propen-1-ol, 2-(4,8-dimethyl-3,7-nonadienyl)-2-propen-1-ol or 2-(4,8,12-trimethyl-3,7,11-trideca-trienyl)-2-propen-1-ol.

In the case of the $R^2$-substituted acrolein acetals ($X$=—CH $(OR^8)_2$), $R^8$ is a $C_1$–$C_4$-alkyl radical as described above for $R^1$, in particular methyl, or the two $R^8$ radicals are a $C_2$–$C_6$-alkylene radical which links the two oxygen atoms to form a cyclic acetal and is optionally branched or carries up to two carboxyl groups, cyclohexyl or phenyl radicals. Preferred $C_2$–$C_6$-alkylene radicals are ethylene, propylene, butylene or neopentylene. Preferred $C_2$–$C_6$-alkylene radicals carrying up to two carboxyl groups, cyclohexyl or phenyl radicals are ethylene radicals substituted in position 1 and/or 2 by said radicals. Symmetrically substituted $C_2$ linkers are preferably those listed below, where the linkage points are indicated by a line showing the stereochemistry:

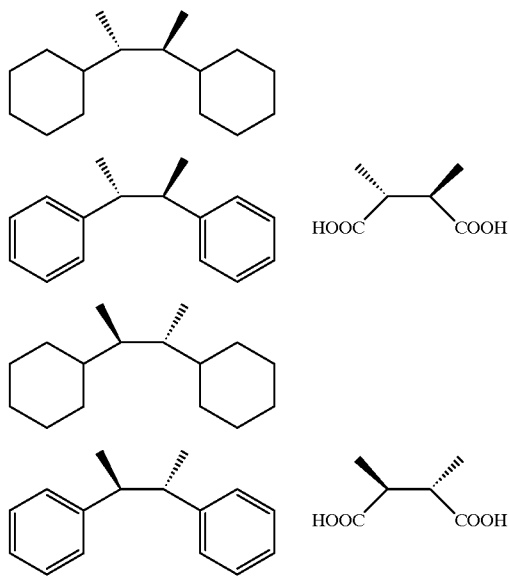

Preferred substituted acrolein acetals of the general formula II are accordingly 2-methyl-3,3-dimethoxypropene, 2-methyl-3,3-diethoxypropene, 2-methyl-3,3-dipropoxypropene, 2-methyl-3,3-dibutoxypropene, 2-(4,8,12-trimethyltridecyl)-3,3-dimethoxypropene, 2-(4,8,12-trimethyltridecyl)-3,3-diethoxypropene, 2-(4,8,12-trimethyltridecyl)-3,3-dipropoxypropene, 2-(4,8,12-trimethyltridecyl)-3,3-dibutoxypropene, 2-(4,8,12-trimethyltridecyl)-3,3-dimethoxypropene, 2-(4,8,12-trimethyltridecyl)-3,3-diethoxypropene, 2-(4,8,12-trimethyltridecyl)-3,3-dipropoxypropene, 2-(4,8,12-trimethyltridecyl)-3,3-dibutoxypropene, 2-(4-methyl-3-pentenyl)-3,3-dimethoxypropene, 2-(4-methyl-3-pentenyl)-3,3-diethoxypropene, 2-(4-methyl-3-pentenyl)-3,3-dipropoxypropene, 2-(4-methyl-3-pentenyl)-3,3-dibutoxypropene, 2-(4,8-dimethyl-3,7-nonadienyl)-3,3-dimethoxypropene, 2-(4,8-dimethyl-3,7-nonadienyl)-3,3-diethoxypropene, 2-(4,8-dimethyl-3,7-nonadienyl)-3,3-dipropoxypropene, 2-(4,8-dimethyl-3,7-nonadienyl)-3,3-dibutoxypropene, 2-(4,8,12-trimethyl-3,7,11-tridecatrienyl)-3,3-dimethoxypropene, 2-(4,8,12-trimethyl-3,7,11-tridecatrienyl)-3,3-diethoxypropene, 2-(4,8,12-trimethyl-3,7,11-tridecatrienyl)-3,3-dipropoxypropene, 2-(4,8,12-trimethyl-3,7,11-tridecatrienyl)-3,3-dibutoxypropene, 2-(1-methylvinyl)-4,5-dimethyl[1,3]dioxane, 2-(1-(4,8,12-trimethyltridecyl)vinyl)-4,5-dimethyl[1,3]dioxane, 2-(1-(4-methyl-3-pentenyl)vinyl)-4,5-dimethyl[1,3]dioxane, 2-(1-(4,8-dimethyl-3,7-nonadienyl)vinyl)-4,5-dimethyl[1,3]-dioxane, 2-(1-(4,8,12-trimethyl-3,7,11-tridecatrienyl)vinyl)-4,5-dimethyl[1,3]dioxane, 2-(1-methylvinyl)-4,5-dicyclohexyl-[1,3]-dioxolane, 2-(1-(4,8,12-trimethyltridecyl)vinyl)-4,5-dicyclo-hexyl[1,3]dioxolane, 2-(1-(4-methyl-3-pentenyl)vinyl)-4,5-dicyclohexyl-[1,3]dioxolane, 2-(1-(4,8-dimethyl-3,7-nonadienyl)vinyl)-4,5-dicyclohexyl-[1,3]-dioxolane, 2-(1-(4,8,12-trimethyl-3,7,11-tridecatrienyl)vinyl)-4,5-dicyclo-hexyl-[1,3]dioxolane, 2-(1-methylvinyl)-[4R,5R]-4,5-dicyclohexyl-[1,3]dioxolane, 2-(1-(4,8,12-trimethyltridecyl)vinyl)-[4R,5R]-4,5-dicyclohexyl-[1,3]dioxolane, 2-(1-(4-methyl-3-pentenyl)-vinyl)-[4R,5R]-4,5-dicyclohexyl-[1,3]dioxolane, 2-(1-(4,8-dimethyl-3,7-nonadienyl)vinyl)-[4R,5R]-4,5-dicyclo-hexyl-[1,3]dioxolane, 2-(1-(4,8,12-trimethyl-3,7,11-tridecatrienyl)vinyl)-[4R,5R]-4,5-dicyclohexyl-[1,3]dioxolane, 2-(1-methylvinyl)-[4S,5S]-4,5-dicyclohexyl-[1,3]dioxolane, 2-(1-(4,8,12-trimethyltridecyl)vinyl)-[4S,5S]-4,5-dicyclohexyl-[1,3]dioxolane, 2-(1-(4-methyl-3-pentenyl)vinyl)-[4S,5S]-4,5-dicyclohexyl-[1,3]dioxolane, 2-(1-(4,8-dimethyl-3,7-nonadienyl)vinyl)-4,5-dicyclohexyl-[1,3]dioxolane, 2-(1-(4,8,12-trimethyl-3,7,11-tridecatrienyl)vinyl)-[4S,5S]-4,5-dicyclohexyl-[1,3]dioxolane, 2-(1-methylvinyl)-4,5-diphenyl-[1,3]dioxolane, 2-(1-(4,8,12-trimethyltridecyl)vinyl)-4,5-diphenyl-[1,3]dioxolane, 2-(1-(4-methyl-3-pentenyl)vinyl)-4,5-diphenyl-[1,3]dioxolane, 2-(1-(4,8-dimethyl-3,7-nonadienyl)-vinyl)-4,5-diphenyl-[1,3]dioxolane, 2-(1-(4,8,12-trimethyl-3,7,11-tridecatrienyl)vinyl)-4,5-diphenyl-[1,3]-dioxolane, 2-(1-methylvinyl)-[4R,5R]-4,5-diphenyl-[1,3]dioxolane, 2-(1-(4,8,12-trimethyltridecyl)vinyl)-[4R,5R]-4,5-diphenyl-[1,3]-dioxolane, 2-(1-(4-methyl-3-pentenyl)vinyl)-[4R,5R]-4,5-diphenyl-[1,3]dioxolane, 2-(1-(4,8-dimethyl-3,7-nonadienyl)-vinyl)-[4R,5R]-4,5-diphenyl-[1,3]dioxolane, 2-(1-(4,8,12-trimethyl-3,7,11-tridecatrienyl)vinyl)-[4R,5R]-4,5-diphenyl-[1,3]dioxolane, 2-(1-methylvinyl)-[4S,5S]-4,5-diphenyl-[1,3]dioxolane, 2-(1-(4,8,12-trimethyltridecyl)vinyl)-[4S,5S]-4,5-diphenyl-[1,3]dioxolane, 2-(1-(4-methyl-3-pentenyl)vinyl)-[4S,5S]-4,5-diphenyl-[1,3]dioxolane, 2-(1-(4,8-dimethyl-3,7-nonadienyl)vinyl)-4,5-diphenyl-[1,3]dioxolane, 2-(1-(4,8,12-trimethyl-3,7,11-tridecatrienyl)vinyl)-[4S,5S]-4,5-diphenyl-[1,3]dioxolane, 2-(1-methylvinyl)-[1,3]dioxolane-4,5-dicarboxylic acid, 2-(1-(4,8,12-trimethyltridecyl)vinyl)-[1,3]dioxolane-4,5-dicarboxylic acid, 2-(1-(4-methyl-3-pentenyl)-vinyl)- [1,3]dioxolane-4,5-dicarboxylic acid, 2-(1-(4,8-dimethyl-3,7-nonadienyl)vinyl)-[1,3]dioxolane-4,5-dicarboxylic acid, 2-(1-(4,8,12-trimethyl-3,7,11-tridecatrienyl)vinyl)-[1,3]-dioxolane-4,5-dicarboxylic acid, 2-(1-methylvinyl)- [1,3]- dioxolane-[4R,5R]-4,5-dicarboxylic acid, 2-(1-(4,8,12-trimethyltridecyl)vinyl)-[1,3]dioxolane-[4R,5R]-4,5-dicarboxylic acid, 2-(1-(4-methyl-3-pentenyl)vinyl)-[1,3]-dioxolane-[4R, 5R]-4,5-dicarboxylic acid, 2-(1-(4,8-dimethyl-3,7-nonadienyl)vinyl)-[1,3]dioxolane-[4R,5R]-4,5-dicarboxylic acid, 2-(1-(4,8,12-trimethyl-3,7,11-tridecatrienyl)vinyl)-[1,3]-dioxolane-[4R,5R]-4,5-dicarboxylic acid, 2-(1-methylvinyl)-[1,3]dioxolane-[4S,5S]-4,5-dicarboxylic acid, 2-(1-(4,8,12-trimethyltridecyl) vinyl)-[1,3]dioxolane-[4S,5S]-4,5-dicarboxylic acid, 2-(1-(4-methyl-3-pentenyl)vinyl)-[1,3]-dioxolane-[4S,5S]-4,5-dicarboxylic acid, 2-(1-(4,8-dimethyl-3,7-nonadienyl)vinyl)-[1,3]dioxolane-[4S,5S]-4,5-dicarboxylic acid or 2-(1-(4,8,12-trimethyl-3,7,11-tridecatrienyl)vinyl)-[1,3]dioxolane-[4S,5S]-4,5-dicarboxylic acid.

In the first step of the process according to the invention, the diene component of the general formula I is reacted with the ene component of the general formula II in a 4+2 cycloaddition (hetero-Diels-Alder reaction).

Hetero-Diels-Alder reactions of electron-poor ene components such as acrylates, acroleins, allyl alcohols or crotonates with acrolein or acroleins alkylated at position 1 or 2 are known.

Thus, it is known that equimolar amounts of methyl vinyl ketone and methyl methacrylate can be converted under (hetero-)Diels-Alder conditions (200° C., 2h) into the mixed Diels-Alder product (2-(carboxymethyl)-2,6-dimethyl-3,4-dihydro-2H-pyran) and the methyl vinyl ketone dimer in the ratio 1:1 (B. P. Mundy, R. D. Otzenberger, A. R. DeBernadis, J. Org. Chem., 36, 1971, p. 2390). More recent investigations confirm this result (J. G. Jun, D. W. Lee, Tetrahedron Lett. 1997, 38, p. 8207, last line, to p. 8208, 2nd paragraph). In addition, B. P. Mundy et al. describe in the above publication that the reaction of methyl vinyl ketone with acrolein methylated in position 2 (methacrolein) does not lead to the required hetero-Diels-Alder product, whereas methyl vinyl ketone and acrolein can be converted into the required hetero-Diels-Alder product. Reaction of 1-methylacrolein with 2-methyl-allyl alcohol leads via the hetero-Diels-Alder product to the bicyclic natural substance frontalin (B. P. Mundy, K. B. Lipkowitz, G. W. Dirks, Heterocycles 1977, 6, p. 64, equation 11). Gore et al. were able to show that 2-methyl-1-penten-3-one and methyl crotonate cannot be reacted to give the required regioisomeric hetero-Diels-Alder product, whereas reaction of 2-methyl-1-penten-3-one with methyl methacrylate leads to the required regioisomeric hetero-Diels-Alder product (W. E. Gore, G. T. Pearce, R. M. Silverstein, J. Org. Chem 1976, 41, pp. 603–604). In addition, Smith et al. describe further hetero-Diels-Alder reactions of alkylated acroleins with alkyl-substituted alkyl vinyl ethers and acrylates (U.S. Pat. No. 2,514,168; C. W. Smith, D. G. Norton, S. A. Ballard, J. Am. Chem. Soc. 1951, pp. 5267–5272).

It is known that introduction of radicals with electron donor properties in position 2 of 1-methylacrolein greatly reduces the reactivity of 1-methylacrolein as diene component in a Diels-Alder reaction (D. L. Boger, S. M. Weinreb, Hetero Diels-Alder—Methodology in Organic Synthesis, Academic Press, Inc, 1987, pp. 185 f.). Thus, only one example, the Diels-Alder dimerization of 3-trimethylsilyloxy-3-buten-2-one (position 3 of 3-buten-2-one corresponds to position 2 of 1-methylacrolein), is known in which the dimerization of methylacrolein with a silyloxy radical in position 2 succeeded in a Diels-Alder reaction (S. Murai; I. Ryu, Y. Kadono, H. Katayama, K. Kondo, N. Sonoda, Chem. Lett. 1977, 1219 f.). Mixed Diels-Alder reactions of acroleins having an electron donor as radical in position 2 with dienophiles are known in only a few cases (D. L. Boger, S. M. Weinreb, loc. cit.). The acroleins moreover have in position 2 a phenylthio radical and react exclusively with electron-rich ene components such as ethyl vinyl ether (K. Takaki, M. Yamada, K. Negoro, J. Org. Chem. 1982, 47, 5246–5250). Funk et al. describe a mixed, Yb-catalyzed, hetero-Diels-Alder reaction of an acrolein with a phenylacyloxy radical in position 2 with the electron-rich ene component ethyl vinyl ether (J. Org. Chem. 1996, 61, 2599, Reaction (e)).

The reaction according to the invention of the oxy-functionalized diene component of the formula I with the electron-poor ene component II affords the corresponding, previously unknown, 3,4-dihydro-2H-pyrans of the general formula III.

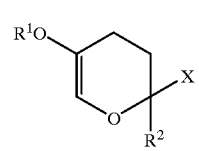

III

The reaction can be carried out under the conditions of the hetero-Diels-Alder reactions known per se (D. L. Boger, S. M. Weinreb, loc. cit.).

The reaction of the two components can take place purely thermally, preferably under autogenous pressure, typically at temperatures from 100° C. to 250° C. or with the addition of Lewis acids such as tin tetrachloride, boron trifluoride, titanium tetrachloride, alkylaluminum dihalides, dialkylaluminum halides, magnesium halides, and halides and trifluoromethanesulfonates of the lanthanides. The reaction can be carried out in organic solvents such as aliphatic, aromatic, optionally halogenated, hydrocarbons or ethers or else without solvent. Preferred organic solvents are xylene, toluene, heptane, THF, dioxane, methylene chloride or chloroform.

The reaction typically takes from 6 to 24 h. The resulting 3,4-dihydro-2H-pyrans can be isolated in a manner known per se, for example by thermal separation processes such as distillation, from the reaction solution.

The radicals $R^1$, $R^2$ and X in preferred substituted 3,4-dihydro-2H-pyrans of the formula III have the following meanings:

$R^1$ $CH_3$ or $COCH_3$, $R^2$ $CH_3$, 4,8,12-trimethyltridecyl or 4,8,12-trimethyl-3,7,11-tridecatrienyl and X CN, COOH, $COOCH_3$, $COO-CH_2-CH_2-OH$, $COO-CH_2-CH_2-Cl$, $COO-CH_2-CH_2-N(CH_3)_2$, CHO, $CH_2OH$, $CH_2OCH_3$ or $CH(OCH_3)_2$ or one of the following structural elements $X_1-X_7$.

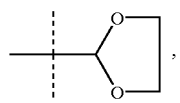

($X_1$)

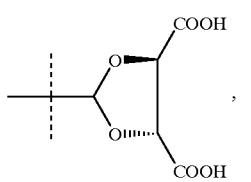
(X₂)
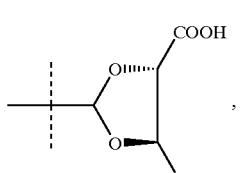
(X₃)
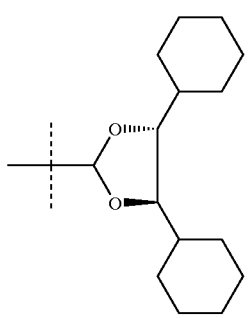
(X₄)
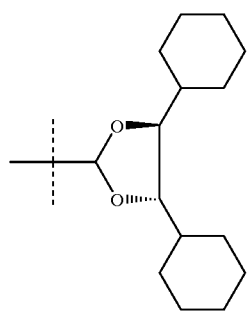
(X₅)
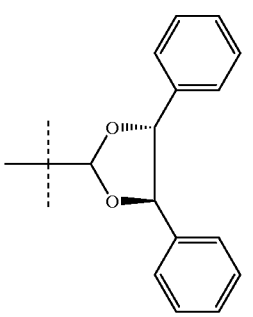
(X₆)
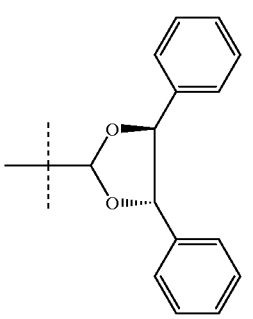
(X₇)
Examples of combinations of radicals in preferred 3,4-dihydro-2H-pyrans of the formula III are the following:
| Compound | R¹ | R² | X |
|---|---|---|---|
| III.001 | CH₃ | CH₃ | CN |
| III.002 | COCH₃ | CH₃ | CN |
| III.003 | CH₃ | ![phytyl chain] | CN |
| III.004 | COCH₃ | ![phytyl chain] | CN |

-continued

| Compound | R¹ | R² | X |
|---|---|---|---|
| III.005 | CH₃ | (farnesyl chain) | CN |
| III.006 | COCH₃ | (farnesyl chain) | CN |
| III.007 | CH₃ | CH₃ | COOH |
| III.008 | COCH₃ | CH₃ | COOH |
| III.009 | CH₃ | (phytyl/saturated chain) | COOH |
| III.0010 | COCH₃ | (phytyl/saturated chain) | COOH |
| III.011 | CH₃ | (farnesyl chain) | COOH |
| III.012 | COCH₃ | (farnesyl chain) | COOH |
| III.013 | CH₃ | CH₃ | COOCH₃ |
| III.014 | COCH₃ | CH₃ | COOCH₃ |
| III.015 | CH₃ | (phytyl/saturated chain) | COOCH₃ |
| III.016 | COCH₃ | (phytyl/saturated chain) | COOCH₃ |
| III.017 | CH₃ | (farnesyl chain) | COOCH₃ |
| III.018 | COCH₃ | (farnesyl chain) | COOCH₃ |
| III.019 | CH₃ | CH₃ | COO—CH₂—CH₂—OH |
| III.020 | COCH₃ | CH₃ | COO—CH₂—CH₂—OH |
| III.021 | CH₃ | (phytyl/saturated chain) | COO—CH₂—CH₂—OH |

-continued

| Compound | R¹ | R² | X |
|---|---|---|---|
| III.022 | COCH₃ | (saturated isoprenoid chain) | COO—CH₂—CH₂—OH |
| III.023 | CH₃ | (triply unsaturated isoprenoid chain) | COO—CH₂—CH₂—OH |
| III.024 | COCH₃ | (triply unsaturated isoprenoid chain) | COO—CH₂—CH₂—OH |
| III.025 | CH₃ | CH₃ | COO—CH₂—CH₂—Cl |
| III.026 | COCH₃ | CH₃ | COO—CH₂—CH₂—Cl |
| III.027 | CH₃ | (saturated isoprenoid chain) | COO—CH₂—CH₂—Cl |
| III.028 | COCH₃ | (saturated isoprenoid chain) | COO—CH₂—CH₂—Cl |
| III.029 | CH₃ | (triply unsaturated isoprenoid chain) | COO—CH₂—CH₂—Cl |
| III.030 | COCH₃ | (triply unsaturated isoprenoid chain) | COO—CH₂—CH₂—Cl |
| III.031 | CH₃ | CH₃ | COO—CH₂—CH₂—N(CH₃)₂ |
| III.032 | COCH₃ | CH₃ | COO—CH₂—CH₂—N(CH₃)₂ |
| III.033 | CH₃ | (saturated isoprenoid chain) | COO—CH₂—CH₂—N(CH₃)₂ |
| III.034 | COCH₃ | (saturated isoprenoid chain) | COO—CH₂—CH₂—N(CH₃)₂ |
| III.035 | CH₃ | (triply unsaturated isoprenoid chain) | COO—CH₂—CH₂—N(CH₃)₂ |
| III.036 | COCH₃ | (triply unsaturated isoprenoid chain) | COO—CH₂—CH₂—N(CH₃)₂ |
| III.037 | CH₃ | CH₃ | CHO |
| III.038 | COCH₃ | CH₃ | CHO |

-continued

| Compound | R¹ | R² | X |
|---|---|---|---|
| III.039 | CH₃ | (branched saturated chain) | CHO |
| III.040 | COCH₃ | (branched saturated chain) | CHO |
| III.041 | CH₃ | (branched triene chain) | CHO |
| III.042 | COCH₃ | (branched triene chain) | CHO |
| III.043 | CH₃ | CH₃ | CH₂OH |
| III.044 | COCH₃ | CH₃ | CH₂OH |
| III.045 | CH₃ | (branched saturated chain) | CH₂OH |
| III.046 | COCH₃ | (branched saturated chain) | CH₂OH |
| III.047 | CH₃ | (branched triene chain) | CH₂OH |
| III.048 | COCH₃ | (branched triene chain) | CH₂OH |
| III.049 | CH₃ | CH₃ | CH₂OCH₃ |
| III.050 | COCH₃ | CH₃ | CH₂OCH₃ |
| III.051 | CH₃ | (branched saturated chain) | CH₂OCH₃ |
| III.052 | COCH₃ | (branched saturated chain) | CH₂OCH₃ |
| III.053 | CH₃ | (branched triene chain) | CH₂OCH₃ |
| III.054 | COCH₃ | (branched triene chain) | CH₂OCH₃ |

-continued

| Compound | R¹ | R² | X |
|---|---|---|---|
| III.055 | CH₃ | CH₃ | CH(OCH₃)₂ |
| III.056 | COCH₃ | CH₃ | CH(OCH₃)₂ |
| III.057 | CH₃ | (phytyl chain) | CH(OCH₃)₂ |
| III.058 | COCH₃ | (phytyl chain) | CH(OCH₃)₂ |
| III.059 | CH₃ | (farnesyl chain) | CH(OCH₃)₂ |
| III.060 | COCH₃ | (farnesyl chain) | CH(OCH₃)₂ |
| III.061 | CH₃ | CH₃ | X₁ |
| III.062 | COCH₃ | CH₃ | X₁ |
| III.063 | CH₃ | (phytyl chain) | X₁ |
| III.064 | COCH₃ | (phytyl chain) | X₁ |
| III.065 | CH₃ | (farnesyl chain) | X₁ |
| III.066 | COCH₃ | (farnesyl chain) | X₁ |
| III.067 | CH₃ | CH₃ | X₂ |
| III.068 | COCH₃ | CH₃ | X₂ |
| III.069 | CH₃ | (phytyl chain) | X₂ |
| III.070 | COCH₃ | (phytyl chain) | X₂ |
| III.071 | CH₃ | (farnesyl chain) | X₂ |

| Compound | R¹ | R² | X |
|---|---|---|---|
| III.072 | COCH$_3$ | (geranylgeranyl chain, triene) | X$_2$ |
| III.073 | CH$_3$ | CH$_3$ | X$_3$ |
| III.074 | COCH$_3$ | CH$_3$ | X$_3$ |
| III.075 | CH$_3$ | (phytyl-type saturated chain) | X$_3$ |
| III.076 | COCH$_3$ | (phytyl-type saturated chain) | X$_3$ |
| III.077 | CH$_3$ | (geranylgeranyl chain, triene) | X$_3$ |
| III.078 | COCH$_3$ | (geranylgeranyl chain, triene) | X$_3$ |
| III.079 | CH$_3$ | CH$_3$ | X$_4$ |
| III.080 | COCH$_3$ | CH$_3$ | X$_4$ |
| III.081 | CH$_3$ | (phytyl-type saturated chain) | X$_4$ |
| III.082 | COCH$_3$ | (phytyl-type saturated chain) | X$_4$ |
| III.083 | CH$_3$ | (geranylgeranyl chain, triene) | X$_4$ |
| III.084 | COCH$_3$ | (geranylgeranyl chain, triene) | X$_4$ |
| III.085 | CH$_3$ | CH$_3$ | X$_5$ |
| III.086 | COCH$_3$ | CH$_3$ | X$_5$ |
| III.087 | CH$_3$ | (phytyl-type saturated chain) | X$_5$ |
| III.088 | COCH$_3$ | (phytyl-type saturated chain) | X$_5$ |

-continued

| Compound | R¹ | R² | X |
|---|---|---|---|
| III.089 | CH₃ | (farnesyl-type chain) | X₅ |
| III.090 | COCH₃ | (farnesyl-type chain) | X₅ |
| III.091 | CH₃ | CH₃ | X₆ |
| III.092 | COCH₃ | CH₃ | X₆ |
| III.093 | CH₃ | (saturated phytyl chain) | X₆ |
| III.094 | COCH₃C | (saturated phytyl chain) | X₆ |
| III.095 | CH₃ | (farnesyl-type chain) | X₆ |
| III.096 | COCH₃ | (farnesyl-type chain) | X₆ |
| III.097 | CH₃ | CH₃ | X₇ |
| III.098 | COCH₃ | CH₃ | X₇ |
| III.099 | CH₃ | (saturated phytyl chain) | X₇ |
| III.100 | COCH₃ | (saturated phytyl chain) | X₇ |
| III.101 | CH₃ | (farnesyl-type chain) | X₇ |
| III.102 | COCH₃C | (farnesyl-type chain) | X₇ |

In the next step of the overall process according to the invention, the 3,4-dihydro-2H-pyrans of the general formula III are reacted with an acid. In this way there is acid-catalyzed elimination of the radical $R^1$ and liberation of the enol, which in turn tautomerizes to the 5-oxotetrahydropyran of the general formula IV

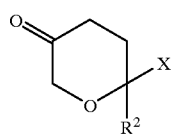

The substituted 3,4-dihydro-2H-pyrans of the general formula III are reacted with an acid in a manner known per se (J. March, Advanced Organic Chemistry, 4$^{th}$ edition, 1992, J. Wiley & sons, pp. 373 f.). Acids mean according to the invention Brönsted acids and their aqueous solutions. Examples which may be mentioned are mineral acids such as HCl, H$_2$SO$_4$, HClO$_4$ and optionally halogenated, i.e. Cl-, Br-, I, F-substituted carboxylic acids such as formic acid, acetic acid, propionic acid, chloroacetic acid, trifluoroacetic acid.

Aqueous acid solutions with a low acid concentration, such as 0.01–12 M, are typically sufficient for converting enol ethers into enols. An example which may be mentioned is a 2M HCl solution.

The reaction is carried out in an organic solvent as mentioned above, preferably in methylene chloride. The duration and temperature of the reaction depend on the radical R$^1$. The reaction is typically carried out at room temperature for 2 to 12 h.

In preferred substituted 5-oxotetrahydropyrans of the general formula IV, the radicals R$^2$ and X have the following meanings:

R$^2$ CH$_3$, 4,8,12-trimethyltridecyl or 4,8,12-trimethyl-3,7,11-tridecatrienyl and X CN, COOH, COOCH$_3$, COO—CH$_2$—CH$_2$—OH, COO—CH$_2$—CH$_2$—Cl, COO—CH$_2$—CH$_2$—N(CH$_3$)$_2$, CHO, CH$_2$OH, CH$_2$OCH$_3$ or CH(OCH$_3$)$_2$ or one of the structural elements X$_1$–X$_7$ as mentioned above for the substituted 3,4-dihydro-2H-pyrans of the formula III.

Examples of radical combinations in preferred substituted 5-oxotetrahydropyrans of the general formula IV are the following:

| Compound | R$^2$ | X |
|---|---|---|
| IV.001 | CH$_3$ | CN |
| IV.002 | | CN |
| IV.003 | | CN |
| IV.004 | CH$_3$ | COOH |
| IV.005 | | COOH |
| IV.006 | | COOH |
| IV.007 | CH$_3$ | COOCH$_3$ |
| IV.008 | | COOCH$_3$ |
| IV.009 | | COOCH$_3$ |
| IV.010 | CH$_3$ | COO—CH$_2$—CH$_2$—OH |
| IV.011 | | COO—CH$_2$—CH$_2$—OH |

-continued

| Compound | R² | X |
|---|---|---|
| IV.012 | (trienyl chain) | COO—CH₂—CH₂—OH |
| IV.013 | CH₃ | COO—CH₂—CH₂—Cl |
| IV.014 | (saturated isoprenoid chain) | COO—CH₂—CH₂—Cl |
| IV.015 | (trienyl chain) | COO—CH₂—CH₂—Cl |
| IV.016 | CH₃ | COO—CH₂—CH₂—N(CH₃)₂ |
| IV.017 | (saturated isoprenoid chain) | COO—CH₂—CH₂—N(CH₃)₂ |
| IV.018 | (trienyl chain) | COO—CH₂—CH₂—N(CH₃)₂ |
| IV.019 | CH₃ | CHO |
| IV.020 | (saturated isoprenoid chain) | CHO |
| IV.021 | (trienyl chain) | CHO |
| IV.022 | CH₃ | CH₂OH |
| IV.023 | (saturated isoprenoid chain) | CH₂OH |
| IV.024 | (trienyl chain) | CH₂OH |
| IV.025 | CH₃ | CH₂OCH₃ |
| IV.026 | (saturated isoprenoid chain) | CH₂OCH₃ |
| IV.027 | (trienyl chain) | CH₂OCH₃ |
| IV.028 | CH₃ | CH(OCH₃)₂ |

-continued

| Compound | R² | X |
|---|---|---|
| IV.029 | (branched saturated C16 chain) | CH(OCH₃)₂ |
| IV.030 | (branched triunsaturated C16 chain) | CH(OCH₃)₂ |
| IV.031 | CH₃ | X₁ |
| IV.032 | (branched saturated C16 chain) | X₁ |
| IV.033 | (branched triunsaturated C16 chain) | X₁ |
| IV.034 | CH₃ | X₂ |
| IV.035 | (branched saturated C16 chain) | X₂ |
| IV.036 | (branched triunsaturated C16 chain) | X₂ |
| IV.037 | CH₃ | X₃ |
| IV.038 | (branched saturated C16 chain) | X₃ |
| IV.039 | (branched triunsaturated C16 chain) | X₃ |
| IV.040 | CH₃ | X₄ |
| IV.041 | (branched saturated C16 chain) | X₄ |
| IV.042 | (branched triunsaturated C16 chain) | X₄ |
| IV.043 | CH₃ | X₅ |
| IV.044 | (branched saturated C16 chain) | X₅ |

-continued

| Compound | R² | X |
|---|---|---|
| IV.045 | (farnesyl-type chain) | X₅ |
| IV.046 | CH₃ | X₆ |
| IV.047 | (saturated isoprenoid chain) | X₆ |
| IV.048 | (partially unsaturated chain) | X₆ |
| IV.049 | CH₃ | X₇ |
| IV.050 | (saturated isoprenoid chain) | X₇ |
| IV.051 | (partially unsaturated chain) | X₇ |

In the next step of the overall process according to the invention, the 5-oxotetrahydropyrans of the general formula IV are reacted with substituted vinyl ketones of the general formula V in a Robinson annulation (J. March, Advanced Organic Chemistry, 4$^{th}$ edition, 1992, J. Wiley & sons, pp. 943–944)

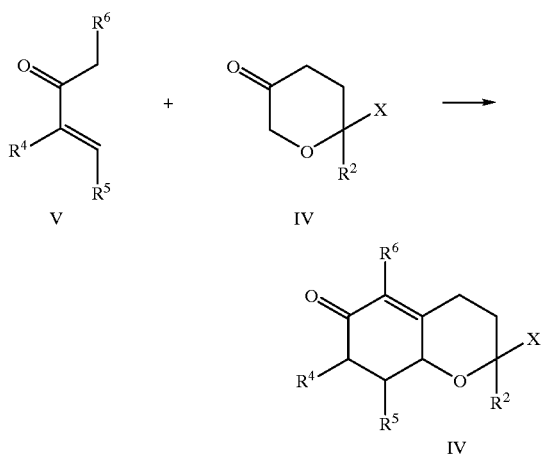

The radicals $R^4$, $R^5$ and $R^6$ are, independently of one another, hydrogen or a $C_1$–$C_4$-alkyl radical as described above for $R^1$, in particular methyl. Preferred substituted vinyl ketones of the general formula V are 4-methyl-4-hexen-3-one ($R^4=R^5=R^6$=methyl),
4-hexen-3-one ($R^4$=hydrogen; $R^5=R^6$=methyl),
3-methyl-3-penten-2-one ($R^4=R^5$=methyl, $R^6$=hydrogen) and
3-penten-2-one ($R^4=R^6$=hydrogen, $R^5$=methyl).

The Robinson annulation can be carried out in a manner known per se (M. E. Jung, Tetrahedron 1976, 32, 3–31; T. Sato et al. Tetrahedron Letters 1990, 31, 1581–1584 and publications cited therein, and F. Eicher, K. Wanner, Arch. der Pharmazie 1984, 317, 958–962).

In a preferred embodiment, the reaction is carried out by the enamine method known per se (G. Storck et al., J. Am. Chem. Soc. 1963, 85, 207). This entails firstly reacting the substituted 5-oxotetrahydropyrans of the general formula IV with secondary amines of the formula VIII $$HN(R^9)_2 \qquad \text{VIII}$$

to give the corresponding enamines of the formula IX

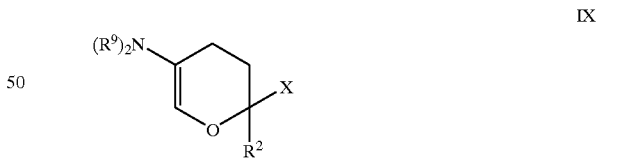

IX

The two $R^9$ radicals are identical or different $C_1$–$C_4$-alkyl radicals as mentioned above for $R^1$, preferably methyl or ethyl, or a phenyl radical or the two $R^9$ radicals represent a $C_2$–$C_6$-alkylene radical, such as ethylene, propylene, butylene, pentylene, neopentylene or hexylene, or a $C_2$–$C_6$-alkylene radical where one or two methylene groups are replaced by oxygen, such as —CH₂—O—CH₂— or —CH₂—CH₂—O—CH₂—CH₂— bridge, to form a cyclic amine.

Preferred secondary amines of the formula VIII are accordingly amines such as dimethylamine, diethylamine, pyrrolidine or morpholine, with pyrrolidine or morpholine being particularly preferred.

This entails reacting the substituted 5-oxotetrahydropyrans of the general formula IV in an organic solvent as mentioned above in the case of the reaction to give the compound of the formula III, firstly with the secondary amine of the formula VIII and a water-binding desiccant such as $MgSO_4$, $Na_2SO_4$ or $TiCl_4$ to give the enamine of the formula IX. In another embodiment, the water which is formed can be removed by azeotropic distillation with the addition of entrainers such as benzene, toluene, pentane or $CH_2Cl_2$. The temperature of the reaction is not critical and is typically room temperature on use of desiccants. The reaction typically takes 12 to 24 h.

The enamines of the formula IX formed from IV are then reacted in a Michael addition with the substituted vinyl ketones of the formula V

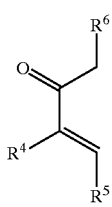

V to give the corresponding keto enamines of the formula X

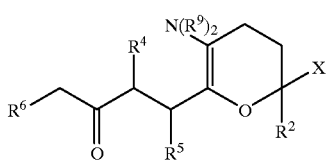

X in a manner known per se (Nelson et al., J. Org. Chem. 1969, 34, 1225).

The keto enamines of the formula X are then converted into the corresponding diketone compounds of the formula XI

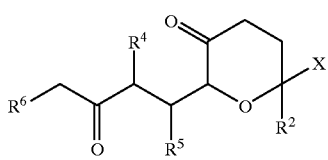

XI by addition of acids, for example mineral acids such as hydrochloric acid or sulfuric acid, or aqueous solutions thereof, and the diketones of the formula XI formed as intermediates are converted into the substituted chromen-6-one derivatives of the general formula VI by addition of a base such as diisopropylethylamine, lithium diethylamide or sodium $C_1$–$C_4$-alcoholates such as sodium methoxide or sodium ethoxide in a manner known per se (M. E. Jung, Tetrahedron 1976, 32, 3; R. E. Ganley, Synthesis 1976, 777).

The radicals $R^2$, $R^4$, $R^5$, $R^6$ and X in preferred substituted chromen-6-one derivatives of the general formula VI have the following meanings:

$R^2$ $CH_3$, 4,8,12-trimethyltridecyl or 4,8,12-trimethyl-3,7,11-tridecatrienyl, $R^4$, $R^5$ and $R^6$ independently of one another hydrogen or $CH_3$ and X CN, COOH, $COOCH_3$, COO—$CH_2$—$CH_2$—OH, COO—$CH_2$—$CH_2$—Cl, COO—$CH_2$—$CH_2$—$N(CH_3)_2$, CHO, $CH_2OH$, $CH_2OCH_3$ or CH $(OCH_3)_2$ or one of the structural elements $X_1$–$X_7$, as mentioned above for the substituted 3,4-dihydro-2H-pyrans of the formula III.

Examples of radical combinations in preferred chromen-6-one derivatives of the formula VI are the following:

| Compound | $R^2$ | $R^4$ | $R^5$ | $R^6$ | X |
|---|---|---|---|---|---|
| VI.001 | $CH_3$ | $CH_3$ | $CH_3$ | $CH_3$ | CN |
| VI.002 | $CH_3$ | H | $CH_3$ | $CH_3$ | CN |
| VI.003 | $CH_3$ | $CH_3$ | $CH_3$ | H | CN |
| VI.004 | $CH_3$ | H | $CH_3$ | H | CN |
| VI.005 | (4,8,12-trimethyltridecyl) | $CH_3$ | $CH_3$ | $CH_3$ | CN |
| VI.006 | (4,8,12-trimethyltridecyl) | H | $CH_3$ | $CH_3$ | CN |
| VI.007 | (4,8,12-trimethyltridecyl) | $CH_3$ | $CH_3$ | H | CN |
| VI.008 | (4,8,12-trimethyltridecyl) | H | $CH_3$ | H | CN |

| Compound | R² | R⁴ | R⁵ | R⁶ | X |
|---|---|---|---|---|---|
| VI.009 | (farnesyl, trimethyl triene) | CH₃ | CH₃ | CH₃ | CN |
| VI.010 | (farnesyl, trimethyl triene) | H | CH₃ | CH₃ | CN |
| VI.011 | (farnesyl, trimethyl triene) | CH₃ | CH₃ | H | CN |
| VI.012 | (farnesyl, trimethyl triene) | H | CH₃ | H | CN |
| VI.013 | CH₃ | CH₃ | CH₃ | CH₃ | COOH |
| VI.014 | CH₃ | H | CH₃ | CH₃ | COOH |
| VI.015 | CH₃ | CH₃ | CH₃ | H | COOH |
| VI.016 | CH₃ | H | CH₃ | H | COOH |
| VI.017 | (saturated phytyl chain) | CH₃ | CH₃ | CH₃ | COOH |
| VI.018 | (saturated phytyl chain) | H | CH₃ | CH₃ | COOH |
| VI.019 | (saturated phytyl chain) | CH₃ | CH₃ | H | COOH |
| VI.020 | (saturated phytyl chain) | H | CH₃ | H | COOH |
| VI.021 | (farnesyl, trimethyl triene) | CH₃ | CH₃ | CH₃ | COOH |
| VI.022 | (farnesyl, trimethyl triene) | H | CH₃ | CH₃ | COOH |
| VI.023 | (farnesyl, trimethyl triene) | CH₃ | CH₃ | H | COOH |
| VI.024 | (farnesyl, trimethyl triene) | H | CH₃ | H | COOH |
| VI.025 | CH₃ | CH₃ | CH₃ | CH₃ | COOCH₃ |

-continued

| Compound | R² | R⁴ | R⁵ | R⁶ | X |
|---|---|---|---|---|---|
| VI.026 | CH₃ | H | CH₃ | CH₃ | COOCH₃ |
| VI.027 | CH₃ | CH₃ | CH₃ | H | COOCH₃ |
| VI.028 | CH₃ | H | CH₃ | H | COOCH₃ |
| VI.029 | (phytyl chain) | CH₃ | CH₃ | CH₃ | COOCH₃ |
| VI.030 | (phytyl chain) | H | CH₃ | CH₃ | COOCH₃ |
| VI.031 | (phytyl chain) | CH₃ | CH₃ | H | COOCH₃ |
| VI.032 | (phytyl chain) | H | CH₃ | H | COOCH₃ |
| VI.033 | (geranylgeranyl chain) | CH₃ | CH₃ | CH₃ | COOCH₃ |
| VI.034 | (geranylgeranyl chain) | H | CH₃ | CH₃ | COOCH₃ |
| VI.035 | (geranylgeranyl chain) | CH₃ | CH₃ | H | COOCH₃ |
| VI.036 | (geranylgeranyl chain) | H | CH₃ | H | COOCH₃ |
| VI.037 | CH₃ | CH₃ | CH₃ | CH₃ | COO—CH₂—CH₂—OH |
| VI.038 | CH₃ | H | CH₃ | CH₃ | COO—CH₂—CH₂—OH |
| VI.039 | CH₃ | CH₃ | CH₃ | H | COO—CH₂—CH₂—OH |
| VI.040 | CH₃ | H | CH₃ | H | COO—CH₂—CH₂—OH |
| VI.041 | (phytyl chain) | CH₃ | CH₃ | CH₃ | COO—CH₂—CH₂—OH |
| VI.042 | (phytyl chain) | H | CH₃ | CH₃ | COO—CH₂—CH₂—OH |
| VI.043 | (phytyl chain) | CH₃ | CH₃ | H | COO—H₂—CH₂—OH |

-continued

| Compound | R² | R⁴ | R⁵ | R⁶ | X |
|---|---|---|---|---|---|
| VI.044 | *phytanyl chain (saturated)* | H | CH₃ | H | COO—CH₂—CH₂—OH |
| VI.045 | *farnesyl chain (triene)* | CH₃ | CH₃ | CH₃ | COO—CH₂—CH₂—OH |
| VI.046 | *farnesyl chain (triene)* | H | CH₃ | CH₃ | COO—CH₂—CH₂—OH |
| VI.047 | *farnesyl chain (triene)* | CH₃ | CH₃ | H | COO—CH₂—CH₂—OH |
| VI.048 | *farnesyl chain (triene)* | H | CH₃ | H | COO—CH₂—CH₂—OH |
| VI.049 | CH₃ | CH₃ | CH₃ | CH₃ | COO—CH₂—CH₂—Cl |
| VI.050 | CH₃ | H | CH₃ | CH₃ | COO—CH₂—CH₂—Cl |
| VI.051 | CH₃ | CH₃ | CH₃ | H | COO—CH₂—CH₂—Cl |
| VI.052 | CH₃ | H | CH₃ | H | COO—CH₂—CH₂—Cl |
| VI.053 | *phytanyl chain (saturated)* | CH₃ | CH₃ | CH₃ | COO—CH₂—CH₂—Cl |
| VI.054 | *phytanyl chain (saturated)* | H | CH₃ | CH₃ | COO—CH₂—CH₂—Cl |
| VI.055 | *phytanyl chain (saturated)* | CH₃ | CH₃ | H | COO—CH₂—CH₂—Cl |
| VI.056 | *phytanyl chain (saturated)* | H | CH₃ | H | COO—CH₂—CH₂—Cl |
| VI.057 | *farnesyl chain (triene)* | CH₃ | CH₃ | CH₃ | COO—CH₂—CH₂—Cl |
| VI.058 | *farnesyl chain (triene)* | H | CH₃ | CH₃ | COO—CH₂—CH₂—Cl |
| VI.059 | *farnesyl chain (triene)* | CH₃ | CH₃ | H | COO—CH₂—CH₂—Cl |

-continued

| Compound | R² | R⁴ | R⁵ | R⁶ | X |
|---|---|---|---|---|---|
| VI.060 | [farnesyl chain] | H | CH₃ | H | COO—CH₂—CH₂—Cl |
| VI.061 | CH₃ | CH₃ | CH₃ | CH₃ | COO—CH₂—CH₂—N(CH₃)₂ |
| VI.062 | CH₃ | H | CH₃ | CH₃ | COO—CH₂—CH₂—N(CH₃)₂ |
| VI.063 | CH₃ | CH₃ | CH₃ | H | COO—CH₂—CH₂—N(CH₃)₂ |
| VI.064 | CH₃ | H | CH₃ | H | COO—CH₂—CH₂—N(CH₃)₂ |
| VI.065 | [phytyl chain] | CH₃ | CH₃ | CH₃ | COO—CH₂—CH₂—N(CH₃)₂ |
| VI.066 | [phytyl chain] | H | CH₃ | CH₃ | COO—CH₂—CH₂—N(CH₃)₂ |
| VI.067 | [phytyl chain] | CH₃ | CH₃ | H | COO—CH₂—CH₂—N(CH₃)₂ |
| VI.068 | [phytyl chain] | H | CH₃ | H | COO—CH₂—CH₂—N(CH₃)₂ |
| VI.069 | [farnesyl chain] | CH₃ | CH₃ | CH₃ | COO—CH₂—CH₂—N(CH₃)₂ |
| VI.070 | [farnesyl chain] | H | CH₃ | CH₃ | COO—CH₂—CH₂—N(CH₃)₂ |
| VI.071 | [farnesyl chain] | CH₃ | CH₃ | H | COO—CH₂—CH₂—N(CH₃)₂ |
| VI.072 | [farnesyl chain] | H | CH₃ | H | COO—CH₂—CH₂—N(CH₃ |
| VI.073 | CH₃ | CH₃ | CH₃ | CH₃ | CHO |
| VI.074 | CH₃ | H | CH₃ | CH₃ | CHO |
| VI.075 | CH₃ | CH₃ | CH₃ | H | CHO |
| VI.076 | CH₃ | H | CH₃ | H | CHO |
| VI.077 | [phytyl chain] | CH₃ | CH₃ | CH₃ | CHO |
| VI.078 | [phytyl chain] | H | CH₃ | CH₃ | CHO |

-continued

| Compound | R² | R⁴ | R⁵ | R⁶ | X |
|---|---|---|---|---|---|
| VI.079 | (saturated isoprenoid chain) | CH₃ | CH₃ | H | CHO |
| VI.080 | (saturated isoprenoid chain) | H | CH₃ | H | CHO |
| VI.081 | (triunsaturated isoprenoid chain) | CH₃ | CH₃ | CH₃ | CHO |
| VI.082 | (triunsaturated isoprenoid chain) | H | CH₃ | CH₃ | CHO |
| VI.083 | (triunsaturated isoprenoid chain) | CH₃ | CH₃ | H | CHO |
| VI.084 | (triunsaturated isoprenoid chain) | H | CH₃ | H | CHO |
| VI.085 | CH₃ | CH₃ | CH₃ | CH₃ | CH₂OH |
| VI.086 | CH₃ | H | CH₃ | CH₃ | CH₂OH |
| VI.087 | CH₃ | CH₃ | CH₃ | H | CH₂OH |
| VI.088 | CH₃ | H | CH₃ | H | CH₂OH |
| VI.089 | (saturated isoprenoid chain) | CH₃ | CH₃ | CH₃ | CH₂OH |
| VI.090 | (saturated isoprenoid chain) | H | CH₃ | CH₃ | CH₂OH |
| VI.091 | (saturated isoprenoid chain) | CH₃ | CH₃ | H | CH₂OH |
| VI.092 | (saturated isoprenoid chain) | H | CH₃ | H | CH₂OH |
| VI.093 | (triunsaturated isoprenoid chain) | CH₃ | CH₃ | CH₃ | CH₂OH |
| VI.094 | (triunsaturated isoprenoid chain) | H | CH₃ | CH₃ | CH₂OH |

-continued

| Compound | R² | R⁴ | R⁵ | R⁶ | X |
|---|---|---|---|---|---|
| VI.095 | (farnesyl-type chain) | CH₃ | CH₃ | H | CH₂OH |
| VI.096 | (farnesyl-type chain) | H | CH₃ | H | CH₂OH |
| VI.097 | CH₃ | CH₃ | CH₃ | CH₃ | CH₂OCH₃ |
| VI.098 | CH₃ | H | CH₃ | CH₃ | CH₂OCH₃ |
| VI.099 | CH₃ | CH₃ | CH₃ | H | CH₂OCH₃ |
| VI.100 | CH₃ | H | CH₃ | H | CH₂OCH₃ |
| VI.101 | (saturated phytyl-type chain) | CH₃ | CH₃ | CH₃ | CH₂OCH₃ |
| VI.102 | (saturated phytyl-type chain) | H | CH₃ | CH₃ | CH₂OCH₃ |
| VI.103 | (saturated phytyl-type chain) | CH₃ | CH₃ | H | CH₂OCH₃ |
| VI.104 | (saturated phytyl-type chain) | H | CH₃ | H | CH₂OCH₃ |
| VI.105 | (farnesyl-type chain) | CH₃ | CH₃ | CH₃ | CH₂OCH₃ |
| VI.106 | (farnesyl-type chain) | H | CH₃ | CH₃ | CH₂OCH₃ |
| VI.107 | (farnesyl-type chain) | CH₃ | CH₃ | H | CH₂OCH₃ |
| VI.108 | (farnesyl-type chain) | H | CH₃ | H | CH₂OCH₃ |
| VI.109 | CH₃ | CH₃ | CH₃ | CH₃ | CH(OCH₃)₂ |
| VI.110 | CH₃ | H | CH₃ | CH₃ | CH(OCH₃)₂ |
| VI.111 | CH₃ | CH₃ | CH₃ | H | CH(OCH₃)₂ |
| VI.112 | CH₃ | H | CH₃ | H | CH(OCH₃)₂ |
| VI.113 | (saturated phytyl-type chain) | CH₃ | CH₃ | CH₃ | CH(OCH₃)₂ |

-continued

| Compound | R² | R⁴ | R⁵ | R⁶ | X |
|---|---|---|---|---|---|
| VI.114 | (C16 isoprenoid chain, saturated) | H | $CH_3$ | $CH_3$ | $CH(OCH_3)_2$ |
| VI.115 | (C16 isoprenoid chain, saturated) | $CH_3$ | $CH_3$ | H | $CH(OCH_3)_2$ |
| VI.116 | (C16 isoprenoid chain, saturated) | H | $CH_3$ | H | $CH(OCH_3)_2$ |
| VI.117 | (C16 isoprenoid chain, triunsaturated) | $CH_3$ | $CH_3$ | $CH_3$ | $CH(OCH_3)_2$ |
| VI.118 | (C16 isoprenoid chain, triunsaturated) | H | $CH_3$ | $CH_3$ | $CH(OCH_3)_2$ |
| VI.119 | (C16 isoprenoid chain, triunsaturated) | $CH_3$ | $CH_3$ | H | $CH(OCH_3)_2$ |
| VI.120 | (C16 isoprenoid chain, triunsaturated) | H | $CH_3$ | H | $CH(OCH_3)_2$ |
| VI.121 | $CH_3$ | $CH_3$ | $CH_3$ | $CH_3$ | $X_1$ |
| VI.122 | $CH_3$ | H | $CH_3$ | $CH_3$ | $x_1$ |
| VI.123 | $CH_3$ | $CH_3$ | $CH_3$ | H | $X_1$ |
| VI.124 | $CH_3$ | H | $CH_3$ | H | $X_1$ |
| VI.125 | (C16 isoprenoid chain, saturated) | $CH_3$ | $CH_3$ | $CH_3$ | $x_1$ |
| VI.126 | (C16 isoprenoid chain, saturated) | H | $CH_3$ | $CH_3$ | $x_1$ |
| VI.127 | (C16 isoprenoid chain, saturated) | $CH_3$ | $CH_3$ | H | $X_1$ |
| VI.128 | (C16 isoprenoid chain, saturated) | H | $CH_3$ | H | $X_1$ |
| VI.129 | (C16 isoprenoid chain, triunsaturated) | $CH_3$ | $CH_3$ | $CH_3$ | $X_1$ |

-continued

| Compound | R² | R⁴ | R⁵ | R⁶ | X |
|---|---|---|---|---|---|
| VI.130 | [farnesyl-type chain] | H | CH₃ | CH₃ | X₁ |
| VI.131 | [farnesyl-type chain] | CH₃ | CH₃ | H | X₁ |
| VI.132 | [farnesyl-type chain] | H | CH₃ | H | X₁ |
| VI.133 | CH₃ | CH₃ | CH₃ | CH₃ | X₂ |
| VI.134 | CH₃ | H | CH₃ | CH₃ | X₂ |
| VI.135 | CH₃ | CH₃ | CH₃ | H | X₂ |
| VI.136 | CH₃ | H | CH₃ | H | X₂ |
| VI.137 | [saturated phytyl-type chain] | CH₃ | CH₃ | CH₃ | X₂ |
| VI.138 | [saturated phytyl-type chain] | H | CH₃ | CH₃ | x2 |
| VI.139 | [saturated phytyl-type chain] | CH₃ | CH₃ | H | X₂ |
| VI.140 | [saturated phytyl-type chain] | H | CH₃ | H | X₂ |
| VI.141 | [farnesyl-type chain] | CH₃ | CH₃ | CH₃ | X₂ |
| VI.142 | [farnesyl-type chain] | H | CH₃ | CH₃ | X₂ |
| VI.143 | [farnesyl-type chain] | CH₃ | CH₃ | H | X₂ |
| VI.144 | [farnesyl-type chain] | H | CH₃ | H | X₂ |
| VI.145 | CH₃ | CH₃ | CH₃ | CH₃ | X₃ |
| VI.146 | CH₃ | H | CH₃ | CH₃ | X₃ |
| VI.147 | CH₃ | CH₃ | CH₃ | H | X₃ |
| VI.148 | CH₃ | H | CH₃ | H | X₃ |

-continued

| Compound | R² | R⁴ | R⁵ | R⁶ | X |
|---|---|---|---|---|---|
| VI.149 | (phytyl chain) | CH₃ | CH₃ | CH₃ | X₃ |
| VI.150 | (phytyl chain) | H | CH₃ | CH₃ | X₃ |
| VI.151 | (phytyl chain) | CH₃ | CH₃ | H | X₃ |
| VI.152 | (phytyl chain) | H | CH₃ | H | X₃ |
| VI.153 | (geranylgeranyl chain) | CH₃ | CH₃ | CH₃ | X₃ |
| VI.154 | (geranylgeranyl chain) | H | CH₃ | CH₃ | X₃ |
| VI.155 | (geranylgeranyl chain) | CH₃ | CH₃ | H | X₃ |
| VI.156 | (geranylgeranyl chain) | H | CH₃ | H | X₃ |
| VI.157 | CH₃ | CH₃ | CH₃ | CH₃ | X₄ |
| VI.158 | CH₃ | H | CH₃ | CH₃ | X₄ |
| VI.159 | CH₃ | CH₃ | CH₃ | H | X₄ |
| VI.160 | CH₃ | H | CH₃ | H | X₄ |
| VI.161 | (phytyl chain) | CH₃ | CH₃ | CH₃ | x4 |
| VI.162 | (phytyl chain) | H | CH₃ | CH₃ | x4 |
| VI.163 | (phytyl chain) | CH₃ | CH₃ | H | X₄ |
| VI.164 | (phytyl chain) | H | CH₃ | H | X₄ |

-continued

| Compound | R² | R⁴ | R⁵ | R⁶ | X |
|---|---|---|---|---|---|
| VI.165 | (farnesyl group) | CH₃ | CH₃ | CH₃ | X₄ |
| VI.166 | (farnesyl group) | H | CH₃ | CH₃ | X₄ |
| VI.167 | (farnesyl group) | CH₃ | CH₃ | H | X₄ |
| VI.168 | (farnesyl group) | H | CH₃ | H | x4 |
| VI.169 | CH₃ | CH₃ | CH₃ | CH₃ | X₅ |
| VI.170 | CH₃ | H | CH₃ | CH₃ | X₅ |
| VI.171 | CH₃ | CH₃ | CH₃ | H | X₅ |
| VI.172 | CH₃ | H | CH₃ | H | X₅ |
| VI.173 | (phytyl group) | CH₃ | CH₃ | CH₃ | X₅ |
| VI.174 | (phytyl group) | H | CH₃ | CH₃ | X₅ |
| VI.175 | (phytyl group) | CH₃ | CH₃ | H | X₅ |
| VI.176 | (phytyl group) | H | CH₃ | H | X₅ |
| VI.177 | (farnesyl group) | CH₃ | CH₃ | CH₃ | X₅ |
| VI.178 | (farnesyl group) | H | CH₃ | CH₃ | X₅ |
| VI.179 | (farnesyl group) | CH₃ | CH₃ | H | X₅ |
| VI.180 | (farnesyl group) | H | CH₃ | H | X₅ |
| VI.181 | CH₃ | CH₃ | CH₃ | CH₃ | X₆ |
| VI.182 | CH₃ | H | CH₃ | CH₃ | X₆ |

-continued

| Compound | R² | R⁴ | R⁵ | R⁶ | X |
|---|---|---|---|---|---|
| VI.183 | CH₃ | CH₃ | CH₃ | H | X₆ |
| VI.184 | CH₃ | H | CH₃ | H | X₆ |
| VI.185 | (phytyl chain) | CH₃ | CH₃ | CH₃ | X₆ |
| VI.186 | (phytyl chain) | H | CH₃ | CH₃ | X₆ |
| VI.187 | (phytyl chain) | CH₃ | CH₃ | H | X₆ |
| VI.188 | (phytyl chain) | H | CH₃ | H | X₆ |
| VI.189 | (geranylgeranyl chain) | CH₃ | CH₃ | CH₃ | X₆ |
| VI.190 | (geranylgeranyl chain) | CH₃ | CH₃ | | X₆ |
| VI.191 | (geranylgeranyl chain) | CH₃ | CH₃ | H | X₆ |
| VI.192 | (geranylgeranyl chain) | H | CH₃ | H | X₆ |
| VI.193 | CH₃ | CH₃ | CH₃ | CH₃ | X₇ |
| VI.194 | CH₃ | H | CH₃ | CH₃ | X₇ |
| VI.195 | CH₃ | CH₃ | CH₃ | H | X₇ |
| VI.196 | CH₃ | H | CH₃ | H | X₇ |
| VI.197 | (phytyl chain) | CH₃ | CH₃ | CH₃ | x7 |
| VI.198 | (phytyl chain) | H | CH₃ | CH₃ | X₇ |
| VI.199 | (phytyl chain) | CH₃ | CH₃ | H | X₇ |
| VI.200 | (phytyl chain) | H | CH₃ | H | X₇ |

-continued

| Compound | R² | R⁴ | R⁵ | R⁶ | X |
|---|---|---|---|---|---|
| VI.201 | ![structure] | CH₃ | CH₃ | CH₃ | X₇ |
| VI.202 | ![structure] | H | CH₃ | CH₃ | x7 |
| VI.203 | ![structure] | CH₃ | CH₃ | H | X₇ |
| VI.204 | ![structure] | H | CH₃ | H | X₇ |

In the last step of the process according to the invention, the chromen-6-one derivatives of the general formula VI are dehydrogenated by addition of dehydrogenating agents such as Pd(C), MnO$_2$, S, Se or DDQ (dichlorodicyanoquinone; 4,5-dichloro-3,6-dioxo-1,4-cyclohexadiene-1,2-dicarbonitrile) in a manner known per se to give the substituted chromans of the general formula VII (R.P. Fu, R. G. Harvey, Chem. Rev. 1978, 78, 317).

The process according to the invention is a novel process for preparing chroman derivatives of the general formula VII. The process moreover makes use of low-cost starting materials. In addition, the process avoids the well-known problem of regioselectivity in electrophilic substitutions on electron-rich aromatic systems in prior art processes and makes it possible to construct a flexible substituent pattern on the aromatic moiety in the chroman structure. Besides this, the process proceeds via novel, easily handled intermediates which in turn are valuable intermediates for novel pharmaceutical agents, flavorings and fragrances, and vitamins and food additives.

The following examples illustrate the invention.

EXAMPLE 1

Preparation of 2-methyl-2-methoxycarbonyl-5-methoxy-3,4-dihydro-2H-pyran (IIIa)

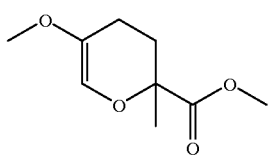

IIIa

1a) Preparation without addition of Lewis acids 0.2 mol of α-methoxyacrolein was dissolved in 100 ml of xylene and then 0.2 mol of methyl methacrylate was added. The mixture was stirred at 180° C. under autogenous pressure for 12 h. Vacuum distillation of the mixture resulted in isolation of 0.08 mol (40% of theory) of the product 2-methyl-2-methoxycarbonyl-5-methoxy-3,4-dihydro-2H-pyran as the colorless oil.

MS(EI): 186 (M+, 48%), 155 (33%), 127 (62%)

¹³C-NMR: 174.5, 140.5, 122.9, 76.1, 55.0, 52.4, 29.8, 25.1, 19.9

1b) Preparation with addition of Lewis acids 0.2 mol of α-methoxyacrolein was dissolved in 100 ml of xylene. Then, while cooling, 10 mmol of tin tetrachloride and then 0.2 mol of methyl methacrylate were added, and the mixture was stirred at 120° C. under autogenous pressure for 12 h. Vacuum distillation of the mixture resulted in isolation of 32% of theory of the product of 2-methyl-2-methoxycarbonyl-5-methoxy-3,4-dihydro-2H-pyran as a pale yellow oil. See 1a for physical data.

EXAMPLE 2

Preparation of 2-methyl-2-formyl-5-methoxy-3,4-dihydro-2H-pyran (IIIb)

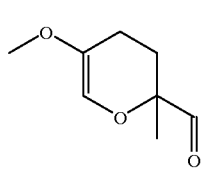

IIIb 0.2 mol of α-methoxyacrolein was dissolved in 100 ml of xylene and then 0.2 mol of methacrolein was added. The mixture was stirred at 180° C. under autogenous pressure for 12 h. Vacuum distillation of the mixture resulted in isolation of 0.11 mol (55% of theory) of the product 2-methyl-2-formyl-5-methoxy-3,4-dihydro-2H-pyran as a colorless oil.

MS(CI): 156 (M+, 12%), 141 (14%), 87 (100%)

EXAMPLE 3

Preparation of 2-methyl-2-hydroxymethyl-5-methoxy-3,4-dihydro-2H-pyran (IIIc)

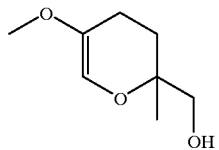

IIIc 0.2 mol of α-methoxyacrolein was dissolved in 100 ml of xylene and then 0.2 ml of methallyl alcohol was added. The mixture was stirred at 180° C. under autogenous pressure for 12 h. Vacuum distillation of the mixture resulted in isolation of 0.15 mol (75% of theory) of the product 2-methyl-2-hydroxymethyl-5-methoxy-3,4-dihydro-2H-pyran as a colorless oil.

MS(CI): 158 (M+, 4%), 141 (9%), 127 (33%), 87 (100%)

EXAMPLE 4

Preparation of 2-hydroxyethyl 2-methyl-5-methoxy-3,4-dihydro-2H-pyran-2-carboxylate (IIId)

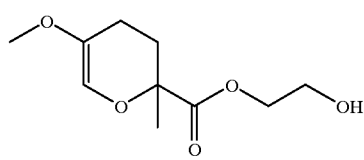

IIId 0.2 mol of α-methoxyacrolein was dissolved in 100 ml of xylene and then 0.2 mol of 2-hydroxyethyl methacrylate was added. The mixture was stirred at 180° C. under autogenous pressure for 12 h. Vacuum distillation of the mixture resulted in isolation of the product 2-hydroxyethyl 2-methyl-5-methoxy-3,4-dihydro-2H-pyran- 2-carboxylate as a colorless oil in a yield of 48%.

MS(EI): 216 (M+, 88%), 127 (100%), 185 (10%), 154 (9%)

EXAMPLE 5

Preparation of 2-chloroethyl 2-methyl-5-methoxy-3,4-dihydro-2H-pyran-2-carboxylate (IIIe)

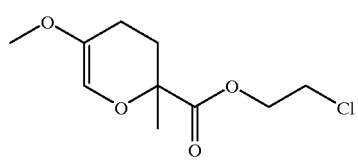

IIIe 0.2 mol of α-methoxyacrolein was dissolved in 100 ml of xylene and then 0.2 mol of 2-chloroethyl methacrylate was added. The mixture was stirred at 180° C. under autogenous pressure for 12 h. Vacuum distillation of the mixture resulted in isolation of the product 2-chloroethyl 2-methyl-5-methoxy-3,4-dihydro-2H-pyran-2-carboxylate as a colorless oil in a yield of 45%.

MS(EI): 234 (M+, 12%), 199 (27%), 113 (100%)

EXAMPLE 6

Preparation of 2-dimethylaminoethyl 2-methyl-5-methoxy-3,4-dihydro-2H-pyran-2-carboxylate (IIIf)

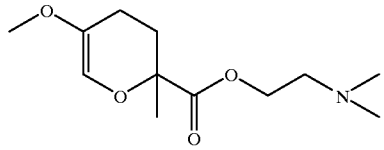

IIIf 0.2 mol of α-methoxyacrolein was dissolved in 100 ml of xylene and then 0.2 mol of 2-dimethylaminoethyl methacrylate was added. The mixture was stirred at 180° C. under autogenous pressure for 12 h. Column chromatography of the mixture resulted in isolation of the product 2-dimethylaminoethyl 2-methyl-5-methoxy-3,4-dihydro-2H-pyran-2-carboxylate in a yield of 52%.

NMR: δ($^{13}$C) in [ppm]: 198.1; 173.6; 140.5; 123.1; 62.6; 57.2; 55.1; 45.2; 29.8; 24.5; 21.6

EXAMPLE 7

Preparation of 2-chloroethyl 2-methyl-5-oxotetrahydropyran-2-carboxylate (IVe) by hydrolyzing 2-chloroethyl 2-methyl-5-methoxy-3,4-dihydro-2H-pyran-2-carboxylate (IIIg)

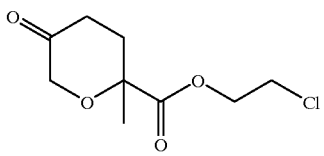

IIIg 3.72 g (20 mmol) of 2-chloroethyl 2-methyl-5-methoxy-3,4-dihydro-2H-pyran-2-carboxylate (IIIe) were dissolved in 20 ml of methylene chloride and, at RT, 20 ml of aqueous HCl solution (2M) were added and the mixture was stirred until precursor was no longer detectable by a TLC check (4 h). The phases were separated. After drying of the organic phase and removal of the solvent, 3.20 g (74%) of 2-chloroethyl 2-methyl-5-oxo-tetrahydropyran-2-carboxylate (IVe) remain as a yellow oil.

MS(EI): 220 (M+, 10%), 151 (4%), 113 (100%)

We claim:

1. A process for preparing substituted chroman derivatives of the general formula VII,

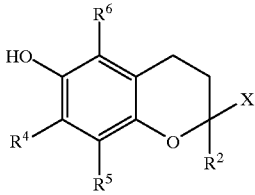

VII where

X is the group —CN, —COOR$^3$, —CHO, —CH$_2$OR$^7$ or —CH(OR$^8$)$_2$, $R^2$ is a $C_1$–$C_{23}$-alkyl, $C_2$–$C_{23}$-alkenyl, $C_6$–$C_{18}$-aryl or $C_7$–$C_{18}$-aralkyl radical, $R^3$ is hydrogen, a $C_1$–$C_4$-alkyl radical, a $C_1$–$C_4$-haloalkyl radical, a $C_1$–$C_4$-hydroxyalkyl radical or a $C_1$–$C_4$-aminoalkyl radical, $R^4$, $R^5$, $R^6$ are, independently of one another, hydrogen or a $C_1$–$C_4$-alkyl radical, $R^7$ is hydrogen or a $C_1$–$C_4$-alkyl radical, $R^8$ is a $C_1$–$C_4$-alkyl radical, or the two radicals are a $C_2$–$C_6$-alkylene radical which links the two oxygen atoms to form a cyclic acetal and is optionally branched or may carry one or two carboxyl groups, cyclohexyl or phenyl radicals, which comprises, in a first step, reacting substituted acroleins of the general formula I,

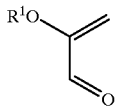

I where $R^1$ is a $C_1$–$C_4$-alkyl, $C_6$–$C_{18}$-aryl, $C_7$–$C_{18}$-aralkyl, $C_1$–$C_4$-acyl, a halogenated $C_1$–$C_4$-acyl radical or another acid-labile protective group for the hydroxyl group, with acrylonitriles, acrylates, acroleins, acrolein acetals, allyl alcohols or allyl ethers of the general formula II

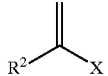

II to give the corresponding 3,4-dihydro-2H-pyrans of the general formula III

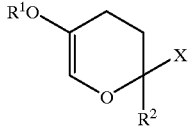

III and, in a second step, reacting the latter with an acid to give the corresponding 5-oxotetrahydropyrans of the general formula IV

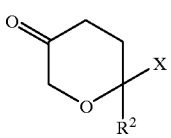

IV and, in a third step, reacting the latter with substituted vinyl ketones of the general formula V

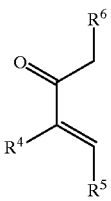

V to give the corresponding chromen-6-one derivatives of the general formula VI

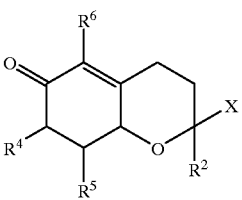

VI and, in a 4th step, dehydrogenating the latter to give the substituted chroman derivatives of the general formula VII.

2. A substituted 3,4-dihydro-2H-pyran of the formula III,

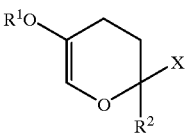

III where $R^1$ is a $C_1$–$C_4$-alkyl, $C_6$–$C_{18}$-aryl, $C_7$–$C_{18}$-aralkyl, $C_1$–$C_4$-acyl, a halogenated $C_1$–$C_4$-acyl radical or another acid-labile protective group for the hydroxyl group, X is the group —CN, —COOR$^3$, —CHO, —CH$_2$OR$^7$ or —CH(OR$^8$)$_2$, $R^2$ is a $C_1$–$C_{23}$-alkyl, $C_2$–$C_{23}$-alkenyl, $C_6$–$C_{18}$-aryl or $C_7$–$C_{18}$-aralkyl radical, $R^3$ is hydrogen, a $C_1$–$C_4$-alkyl radical, a $C_1$–$C_4$-haloalkyl radical, a $C_1$–$C_4$-hydroxyalkyl radical or a $C_1$–$C_4$-aminoalkyl radical, $R^7$ is hydrogen or a $C_1$–$C_4$-alkyl radical, $R^8$ is a $C_1$–$C_4$-alkyl radical, or the two radicals are a $C_2$–$C_6$-alkylene radical which links the two oxygen atoms to form a cyclic acetal and is optionally branched or may carry one or two carboxyl groups, cyclohexyl or phenyl radicals.

3. A substituted 3,4-dihydro-2H-pyran of the formula III as claimed in claim 2, where the substituents have the following meanings:

$R^1$ CH$_3$ or COCH$_3$, $R^2$ CH$_3$, 4,8,12-trimethyltridecyl or 4,8,12-trimethyl-3,7,11-tridecatrienyl and X CN, COOH, COOCH$_3$, COO—CH$_2$—CH$_2$—OH, COO—CH$_2$—CH$_2$—Cl, COO—CH$_2$—CH$_2$—N(CH$_3$)$_2$, CHO, CH$_2$OH, CH$_2$OCH$_3$ or CH(OCH$_3$)$_2$ or one of the following structural elements X$_1$–X$_7$.

(X₁) 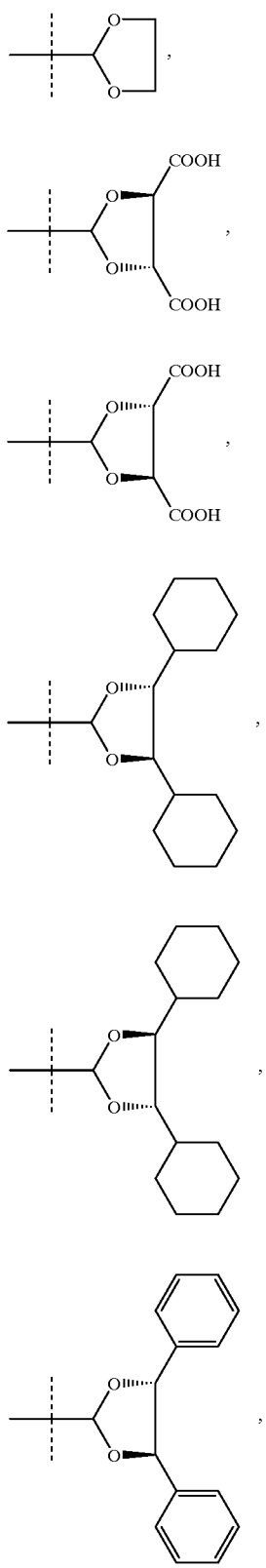

(X₂)

(X₃)

(X₄)

(X₅)

(X₆)

-continued (X₇) 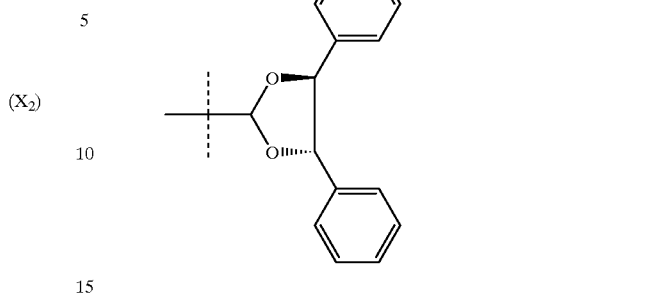

4. A process for preparing substituted 3,4-dihydro-2H-pyrans of the general formula III as claimed in claim 2, which comprises reacting substituted acroleins of the general formula I,

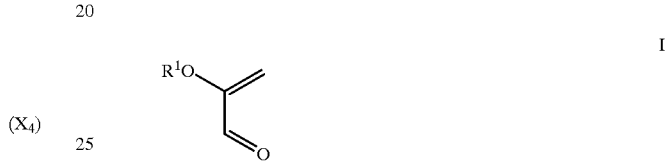

with acrylonitriles, acrylates, acroleins, acrolein acetals, allyl alcohols or allyl ethers of the general formula II,

5. A substituted 5-oxotetrahydropyran of the formula IV,

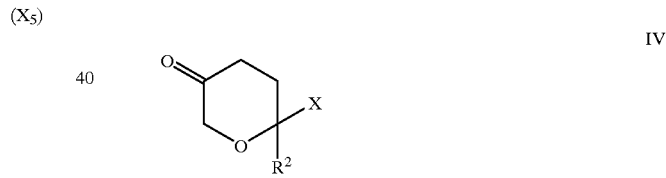

where
X is the group —CN, —COOR³, —CHO, —CH₂OR⁷ or —CH(OR⁸)₂,
$R^2$ is a $C_1-C_{23}$-alkyl, $C_2-C_{23}$-alkenyl, $C_6-C_{18}$-aryl or $C_7-C_{18}$-aralkyl radical,
$R^3$ is hydrogen, a $C_1-C_4$-alkyl radical, a $C_1-C_4$-haloalkyl radical, a $C_1-C_4$-hydroxyalkyl radical or a C1–C4-aminoalkyl radical,
$R^7$ is hydrogen or a $C_1-C_4$-alkyl radical,
$R^8$ is a $C_1-C_4$-alkyl radical, or the two radicals are a $C_2-C_6$-alkylene radical which links the two oxygen atoms to form a cyclic acetal and is optionally branched or may carry one or two carboxyl groups, cyclohexyl or phenyl radicals.

6. A substituted 5-oxotetrahydropyran of the formula IV as claimed in claim 5, where the substituents have the following meanings:
$R^2$ CH₃, 4,8,12-trimethyltridecyl or 4,8,12-trimethyl-3,7,11-tridecatrienyl and X CN, COOH, COOCH₃, COO—CH₂—CH₂—OH, COO—CH₂—CH₂—Cl, COO—CH₂—CH₂—N(CH₃)₂, CHO, CH₂OH, CH₂OCH₃ or CH(OCH₃)₂ or one of the following structural elements $X_1$–$X_7$.

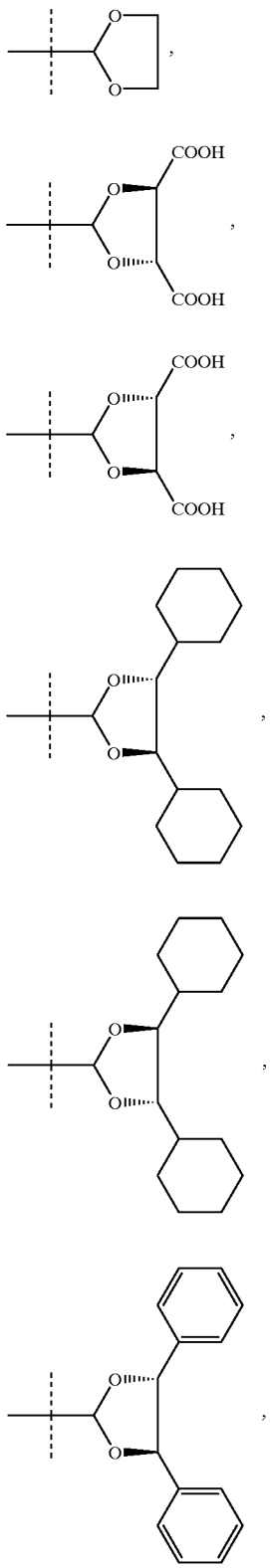

(X₁)

(X₂)

(X₃)

(X₄)

(X₅)

(X₆)

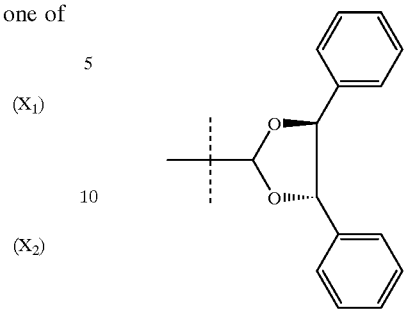

(X₇)

7. A process for preparing substituted 5-oxotetrahydropyrans of the formula IV as claimed in claim 6, which comprises reacting substituted acroleins of the general formula I,

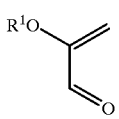

I where
$R^1$ is a $C_1$–$C_4$-alkyl, $C_6$–$C_{18}$-aryl, $C_7$–$C_{18}$-aralkyl, $C_1$–$C_4$-acyl, a halogenated $C_1$–$C_4$-acyl radical or another acid-labile protective group for the hydroxyl group,
with acrylonitriles, acrylates, acroleins, acrolein acetals, allyl alcohols or allyl ethers of the general formula II

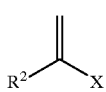

II to give the corresponding 3,4-dihydro-2H-pyrans of the general formula III

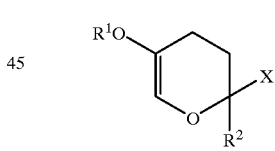

III and, in a second step, converting the latter with an acid into the 5-oxotetrahydropyrans of the formula IV.

8. A substituted chromen-6-one derivative of the formula VI,

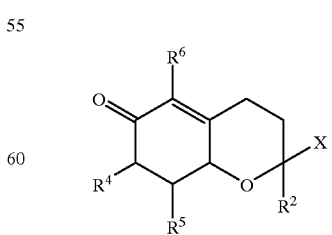

VI where
X is the group —CN, —COOR³, —CHO, —CH₂OR⁷ or —CH(OR⁸)₂, $R^2$ is a $C_1$–$C_{23}$-alkyl, $C_2$–$C_{23}$-alkenyl, $C_6$–$C_{18}$-aryl or $C_7$–$C_{18}$-aralkyl radical, $R^3$ is hydrogen, a $C_1$–$C_4$-alkyl radical, a $C_1$–$C_4$-haloalkyl radical, a $C_1$–$C_4$-hydroxyalkyl radical or a $C_1$–$C_4$-aminoalkyl radical, $R^4$, $R^5$, $R^6$, independently of one another, are hydrogen or a $C_1$–$C_4$-alkyl radical, $R^7$ is hydrogen or a $C_1$–$C_4$-alkyl radical, $R^8$ is a $C_1$–$C_4$-alkyl radical, or the two radicals are a $C_2$–$C_6$-alkylene radical which links the two oxygen atoms to form a cyclic acetal and is optionally branched or may carry one or two carboxyl groups, cyclohexyl or phenyl radicals.

9. A substituted chromen-6-one derivative of the formula VI as claimed in claim 8, where the substituents have the following meanings:

$R^2$ $CH_3$, 4,8,12-trimethyltridecyl or 4,8,12-trimethyl-3,7,11-tridecatrienyl, $R^4$, $R^5$ and $R^6$ independently of one another hydrogen or $CH_3$ and X CN, COOH, COOCH$_3$, COO—CH$_2$—CH$_2$—OH, COO—CH$_2$—CH$_2$—Cl, COO—CH$_2$—CH$_2$—N(CH$_3$)$_2$, CHO, CH$_2$OH, CH$_2$OCH$_3$ or CH(OCH$_3$)$_2$ or one of the following structural elements $X_1$–$X_7$.

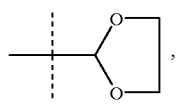

($X_1$)

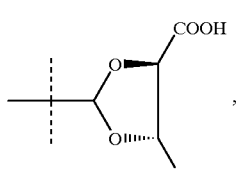

($X_2$)

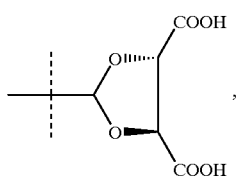

($X_3$)

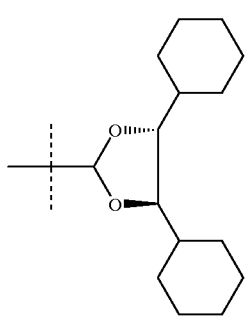

($X_4$)

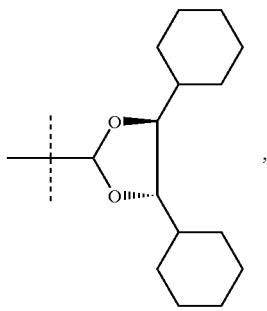

($X_5$)

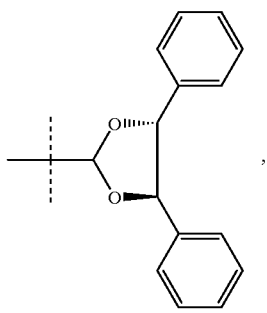

($X_6$)

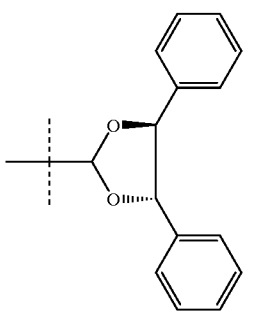

($X_7$)

10. A process for preparing substituted chromen-6-one derivatives of the general formula VI as claimed in claim 8, which comprises reacting substituted 5-oxotetrahydropyrans of the general formula IV

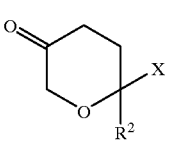

IV with substituted vinyl ketones of the general formula V

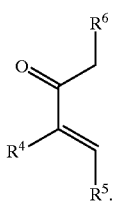

V

11. A process as claimed in claim 10, wherein the substituted 5-oxotetrahydropyrans of the general formula IV

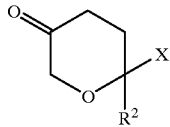

IV are reacted with secondary amines of the formula VIII $HN(R^9)_2$  VIII where $R^9$ is a $C_1$–$C_4$-alkyl or phenyl radical, or the two $R^9$ radicals represent a $C_2$–$C_6$-alkylene or $C_2$–$C_6$-alkoxyalkylene radical bridge to form a cyclic amine, to give the corresponding enamines of the formula IX,

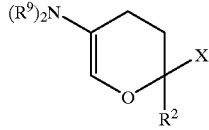

IX the enamines of the formula IX are reacted with the substituted vinyl ketones of the general formula V

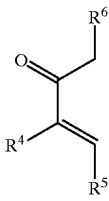

V to give the corresponding keto enamines of the formula X

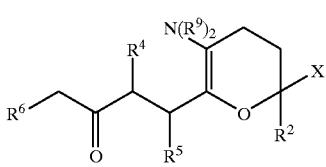

X the keto enamines of the formula X are converted by addition of an acid into the corresponding diketone compounds of the formula XI

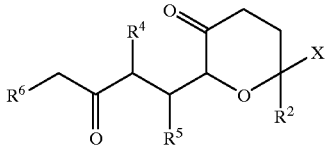

XI and the diketones of the formula XI are converted by addition of a base into the substituted chromen-6-one derivatives of the general formula VI.

* * * * *